(12) United States Patent
Bazzaro et al.

(10) Patent No.: US 10,416,163 B2
(45) Date of Patent: Sep. 17, 2019

(54) METHOD AND TREATMENT OF RECURRING ENDOMETRIAL CANCER WITH AN INHIBITOR OF USP14

(71) Applicant: Regents of the University of Minnesota, Minneapolis, MN (US)

(72) Inventors: Martina Bazzaro, St. Paul, MN (US); Tanya Pulver, Minneapolis, MN (US); Rahel Ghebre, Golden Valley, MN (US); Rachel Isaksson Vogel, Eagan, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/443,417

(22) Filed: Feb. 27, 2017

(65) Prior Publication Data

US 2017/0269091 A1    Sep. 21, 2017

Related U.S. Application Data

(60) Provisional application No. 62/300,494, filed on Feb. 26, 2016.

(51) Int. Cl.
| | | |
|---|---|---|
| *G01N 33/574* | (2006.01) | |
| *A61K 31/55* | (2006.01) | |
| *C12N 15/113* | (2010.01) | |
| *C12N 9/48* | (2006.01) | |
| *C12Q 1/6886* | (2018.01) | |

(52) U.S. Cl.
CPC ....... *G01N 33/57442* (2013.01); *A61K 31/55* (2013.01); *C12N 9/485* (2013.01); *C12N 15/1135* (2013.01); *C12N 15/1137* (2013.01); *C12Q 1/6886* (2013.01); *C12Y 304/19012* (2013.01); *G01N 33/57449* (2013.01); *C12N 2310/12* (2013.01); *C12N 2310/14* (2013.01); *G01N 2333/948* (2013.01)

(58) Field of Classification Search
None
See application file for complete search history.

(56) References Cited

U.S. PATENT DOCUMENTS

2014/0228354 A1*  8/2014  Linder ................. C07D 223/08
                                                      514/217.08

OTHER PUBLICATIONS

Coughlin et al. Small-molecule RA-9 inhibits proteasome-associated DUBs and ovarian cancer in vitro and in vivo via exacerbating unfolded protein responses. Clin. Cancer Res., 20, 3174-3186, 2014. (Year: 2014).*
Selvaraju et al. Inhibition of proteasome deubiquitinase activity: a strategy to overcome resistance to conventional proteasome inhibitors? Drug Resist. Updates, 21-22, 20-29, 2015. (Year: 2015).*
Wang et al., Ubiquitin-specific protease 14 (USP14) regulates cellular proliferation and apoptosis in epithelial ovarian cancer. Med. Oncol. 32, 379, 2015. (Year: 2015).*

* cited by examiner

*Primary Examiner* — Elly-Gerald Stoica
(74) *Attorney, Agent, or Firm* — Schwegman Lundberg & Woessner, P.A.

(57) ABSTRACT

USP14 is a biomarker for recurrent disease and inhibition of USP14 is of therapeutic benefit for women with endometrial or ovarian cancer.

6 Claims, 17 Drawing Sheets

METHOD AND TREATMENT OF RECURRING ENDOMETRIAL CANCER WITH AN INHIBITOR OF USP14

PRIORITY

This application claims the benefit of priority from U.S. Provisional Patent Application Ser. No. 62/300,494, filed on Feb. 26, 2016, which is herein incorporated by reference.

GOVERNMENT FUNDING

This invention was made with government support under W81XWH-10-1-0067 awarded by the Dept. of the Army and UL1TR000114 awarded by the National Institutes of Health. The government has certain rights in the invention.

BACKGROUND OF THE INVENTION

Endometrial adenocarcinoma is the most common gynecologic malignancy in the United States and is classified into two main categories based primarily on grade. Type I cancers are typically less aggressive and account for three fourths of endometrial cancer cases. These often can be cured with surgery alone. Type II cancers are more high risk with worse prognosis. Women diagnosed with Type II cancers require a combination of surgery, radiation and or chemotherapy treatment. Unfortunately, a significant (approx. 15%) percentage of early stage Type I endometrial cancer recurs for reasons that are not fully elucidated. Recurrence is often accompanied by chemo-resistance and high mortality.

SUMMARY OF THE INVENTION

Disclosed herein is the discovery that USP14 expression correlates with recurrence of endometrial and/or ovarian cancer, independent of Type. The studies described herein show that after taking into account other known risk factors for recurrence, namely disease grade, stage, and lymphovascular space invasion (LVSI) status, higher USP14 staining intensity was associated with increased risk of recurrence (p=0.01). Specifically, a woman with a USP14 staining intensity of 3 compared to a woman with a USP14 staining intensity of 2 (with grade, stage and LVSI status equal) is more than 6 times more likely to recur (OR=6.9 (95% CI: 1.6-29.6)).

Molecular profile markers such as USP14 can inform the care of endometrial or ovarian cancer patients, specifically regarding use of adjuvant therapy. USP14 staining intensity can be determined pre-operatively via biopsy (along with grade) and therefore can also be used to guide surgical decisions including lymph node dissection and route. When compared to grade alone, knowing USP14 staining grade resulted in increased prediction of recurrence in the patient population (area under the curve of highest grade only=0.64 compared to area under the curve of grade and USP14 staining highest grade=0.77, p=0.02).

One embodiment of the invention provides a method to determine the likelihood of recurrence of endometrial or ovarian cancer in a subject suffering from endometrial or ovarian cancer comprising a) measuring the amount of USP14 in a biological sample obtained from the subject; and b) comparing the measured amount of the marker with a standard amount/control, wherein an increased amount of USP14 relative to the control is indicative of an increased likelihood of recurrence of endometrial and/or ovarian cancer in the subject. In one embodiment, the subject is human. In another embodiment, the USP14 is USP14 protein or mRNA. In one embodiment, the USP14 protein or mRNA is detected using a method selected from the group consisting of ELISA, immunoassay, immunofluorescence, immunohistochemistry, immunoprecipitation, northern blot, western blot. PCR, mass spectrometry, and surface Plasmon resonance. In one embodiment, the sample is tissue biopsy. One embodiment further provides measuring, along with USP14, the protein and/or mRNA level of at least one or a combination of L1CAM (L1 Cell Adhesion Molecule; Accession numbers NM_000425 and NP_000416), Ki67 (Accession numbers NM_001145966 and NP_001139438) and/or UNC45A (Protein unc-45 homolog A; Accession numbers NM_001039675 and NP_001034764) in a sample to determine the likelihood of recurrence of endometrial cancer in a subject suffering from endometrial cancer and treat if needed.

One embodiment provides a method to treat endometrial or ovarian cancer in a subject in need thereof comprising administering an effective amount of a pharmaceutical composition comprising an agent which inhibits the activity of USP14 so as to treat the endometrial and/or ovarian cancer. In one embodiment, the cancer is chemoresistant (and can be treated with a USP14 inhibitor or with the USP14 inhibitor in combination with chemotherapy). Another embodiment provides a method to selectively treat a subject having endometrial or ovarian cancer, which comprises selectively administering to the subject an agent which inhibits the activity of USP14, on the basis of said subject having previously been determined to have increased expression of USP14 as compared to a control (in one embodiment, one or more inhibitors of USP14 are can be used as maintenance therapy to prevent cancer recurrence). In one embodiment, the subject is human. In another embodiment, the agent is a protein, nucleic acid and/or small molecule. In one embodiment, the nucleic acid is a siRNA or a ribozyme directed against USP14 mRNA. In one embodiment, the protein is an antibody. In another embodiment, the small molecule is VLX1570 or RA-9 (Coughlin et al. Clin Cancer Res (2014)). One embodiment further comprises surgery, chemotherapy, and/or radiation. In one embodiment, the surgery comprises lymph node dissection.

One embodiment provides a method to screen for an agent that inhibits USP14 activity comprising contacting USP14 or cells comprising USP14 and determining whether the agent inhibits USP14 activity relative to USP14 or cells comprising USP14 which have not been contacted with the agent.

Another embodiment provides a kit comprising a container comprising an agent for determining the level of USP14 in a sample, a control, and instructions to provide guidance for carrying out the assay and for making a determination based upon that assay. In one embodiment, the agent is an antibody or antigen-binding fragment thereof against USP14.

Various aspects and embodiments of the invention are described in further detail below.

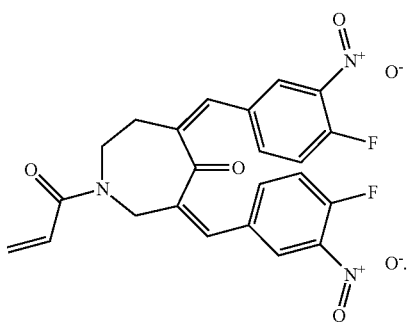

DETAILED DESCRIPTION OF THE INVENTION

Figure 1A:
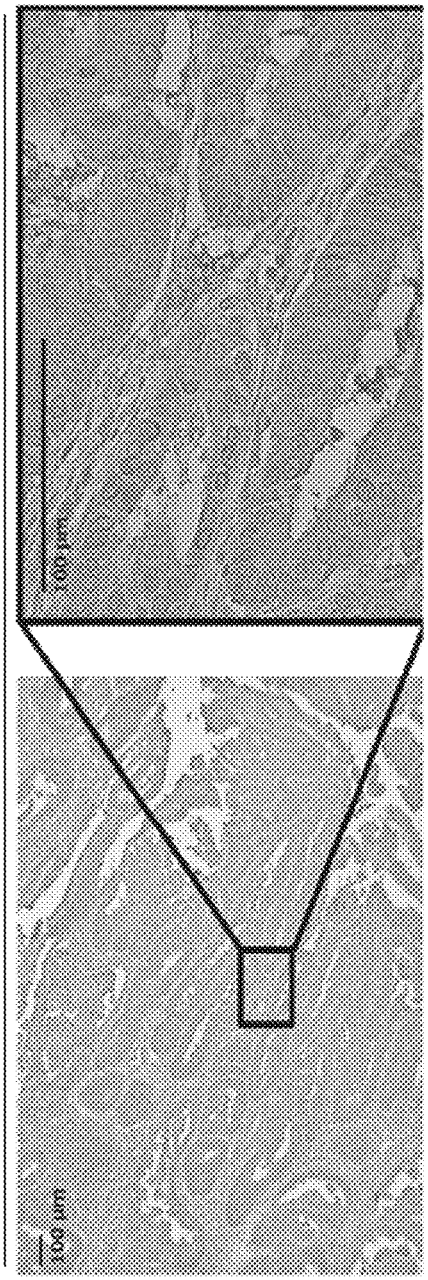
FIGS. 1A-C demonstrate that USP14 is overexpressed at diagnosis of endometrial adenocarcinoma among patients who eventually recur. Immunohistochemical staining of USP14 in endometrial cancer tumors. Representative example patient with endometrial cancer with (A) weak staining in a patient who did not recur and (B) intense staining in a patient who did recur within 36 months. (C). Boxplots depicting the average USP14 staining intensity at diagnosis for patients with endometrial adenocarcinoma who did not recur (left) and those who recurred (right) within 36 months of diagnosis. The median USP14 staining intensity was higher among those who recurred (p=0.02). Symbols on the boxplot are as follows: Box=1st to 3rd (Q1-Q3) Quartiles. Line inside box=Median.

Nearly 80% of endometrial cancer patients have low risk. Identifying a subset of them with molecular profiling offered by markers such as UPS 14 can sub-select an otherwise low risk patient that would potentially alter surgical intervention and make them eligible for adjuvant treatment. Currently there is no standardized molecular profiling available for endometrial cancer tissue in clinical use, beyond routine known pathology determined risk factors. In the absence of other high risk pathology determined risk factors for recurrence, most cases of early-stage low-risk endometrial cancers are treated with surgery alone. Provided herein is the solution to the problem of not being able to stratify endometrial cancer patients based on the likelihood that their cancer will recur.

USP14 expression is a biomarker for recurrence risk in early-stage endometrial cancer, and as such has major implications with regard to the prognosis and treatment of patients who by current standards would warrant no further initial treatment besides surgery. Testing for USP14 expression can be accomplished relatively inexpensively and easily using the proposed techniques described herein, for example, the preoperative setting. This means that patients found preoperatively to have low USP14 expression could potentially be spared aggressive surgery including lymph node dissection and the morbidity associated with that operation. In contrast, women with high levels of expression could be identified and advised to undergo adjuvant therapy with radiation or chemotherapy to help minimize their risk of recurrence.

Thus, disclosed herein is molecular profiling, as part of pre-treatment and surgical planning, for endometrial cancer patients and as part of the treatment algorithm for post-surgery decision making in low risk and high risk endometrial cancer patients. In addition, many women undergo endometrial biopsy testing for possible risk of endometrial cancer and USP14 can be used to test for development of cancer.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment," "an embodiment," etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only." and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is di-substituted.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims. "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including," "includes," "having." "has." "with," or variants thereof, are intended to be inclusive similar to the term "comprising."

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group.

Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "marker" refers to a molecule (typically protein, nucleic acid, carbohydrate, or lipid) that is expressed in an endometrial cell from a women with endometrial cancer, expressed on the surface of an endometrial cell from a woman with endometrial cancer, or secreted by an endometrial cell from a woman with endometrial cancer in comparison to a cell from a woman who does not have endometrial cancer, and which is useful for the diagnosis of endometrial cancer, for providing a prognosis, and for preferential targeting of a pharmacological agent to the endometrial cell/marker. Oftentimes, such markers are molecules that are overexpressed in an endometrial cell from a woman with endometrial cancer in comparison to a cell from a woman without endometrial cancer, for instance, 1-fold overexpression, 2-fold overexpression, 3-, 4-, 5-, 6-, 7-, 8-, 9-, or 10-fold overexpression or more fold-overexpression in comparison to a cell from a woman without endometrial cancer. Further, a marker can be a molecule that is inappropriately synthesized in the endometrial cell of a woman with endometrial cancer, for instance, a molecule that contains deletions, additions, or mutations in comparison to the molecule expressed in a cell from a woman without endometrial cancer. Alternatively, such biomarkers are molecules that are under-expressed in an endometrial cell from a woman with endometrial cancer in comparison to a cell from a woman without endometrial cancer, for instance, 1-fold under-expression, 2-fold under-expression, 3-, 4-, 5-, 6-, 7-, 8-, 9-, or 10-fold under-expression, or more fold-overexpression in comparison to a cell from a woman without endometrial cancer.

It will be understood by the skilled artisan that markers may be used in combination with other markers or tests for any of the uses, e.g., prediction or diagnosis, disclosed herein.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, endometrial tissue, the uterine fundus, thyroid tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent. e.g., guinea pig, rat, Mouse: rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., endometrial, etc.), the size and type of the tissue, among other factors. Representative biopsy techniques include, but are not limited to, excisional biopsy, incisional biopsy, needle biopsy, surgical biopsy, and bone marrow biopsy. An "excisional biopsy" refers to the removal of an entire endometrial tissue mass with a small margin of non-endometrial tissue surrounding it. An "incisional biopsy" refers to the removal of a wedge of endometrial tissue. Biopsy techniques are discussed, for example, in Harrison's Principles of Internal Medicine. Kasper, et al., eds., 16th ed., 2005. Chapter 70, and throughout Part V.

"Detecting" refers to determining the presence, absence, or amount of an analyte in a sample, and can include quantifying the amount of the analyte in a sample or per cell in a sample.

The terms "overexpress," "overexpression," "overexpressed," or "up-regulated" interchangeably refer to a protein or nucleic acid (RNA) that is transcribed or translated at a detectably greater level, usually in an endometrial cell from a woman with endometrial cancer, in comparison to a cell from a woman without endometrial cancer. The term includes overexpression due to transcription, post transcriptional processing, translation, post-translational processing, cellular localization (e.g., organelle, cytoplasm, nucleus, cell surface), and RNA and protein stability, as compared to a cell from a woman without endometrial cancer. Overexpression can be detected using conventional techniques for detecting mRNA (i.e., Q-PCR. RT-PCR. PCR, hybridization) or proteins (i.e., ELISA, immunohistochemical techniques). Overexpression can be 10%, 20%, 30%, 40%, 50%, 60%, 70%, 80%, 90% or more in comparison to a cell from a woman without endometrial cancer. In certain instances, overexpression is 1-, 2-, 3-, 4-, 5-, 6-, 7-, 8-, 9-, 10-fold, or more higher levels of transcription or translation in comparison to a cell from a woman without endometrial cancer.

The terms "under-express," "under-expression," "under-expressed," or "down-regulated" interchangeably refer to a protein or nucleic acid that is transcribed or translated at a detectably lower level in an endometrial cell from a woman with endometrial cancer, in comparison to a cell from a woman without endometrial cancer. The term includes under-expression due to transcription, post transcriptional processing, translation, post-translational processing, cellular localization (e.g., organelle, cytoplasm, nucleus, cell surface), and RNA and protein stability, as compared to a control. Under-expression can be detected using conventional techniques for detecting mRNA (i.e., Q-PCR, RT-PCR, PCR, hybridization) or proteins (i.e., ELISA, immunohistochemical techniques). Under-expression can be 10%, 20%, 30%, 40%, 50%, 60%, 70%, 80%, 90% or less in comparison to a control. In certain instances, under-expression is 1-, 2-, 3-, 4-, 5-, 6-, 7-, 8-, 9-, 10-fold or more lower levels of transcription or translation in comparison to a control.

The term "differentially expressed," "differentially regulated," or "altered expression" refers generally to a protein or nucleic acid that is overexpressed (upregulated) or underexpressed (downregulated) in one sample compared to at least one other sample, generally in a patient with endometrial cancer, in comparison to a patient without endometrial cancer, in the context of the present invention.

"Therapeutic treatment" or adjuvant treatment refers to chemotherapy, hormonal therapy, radiotherapy, immunotherapy, and biologic (targeted) therapy, as well as with an inhibitor of UPS 14.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art. Science and Technology of Pharmaceutical Compounding (1999); Pickar, Dosage Calculations (1999); and Remington: The Science and Practice of Pharmacy, 20th Edition, 2003. Gennaro, Ed., Lippincott, Williams & Wilkins).

As use herein, the terms "administration of" and or "administering" a compound should be understood to mean providing a compound of the invention or a prodrug of a compound of the invention to a subject in need of treatment.

As used herein. "alleviating a disease or disorder symptom." means reducing the severity of the symptom or the frequency with which such a symptom is experienced by a patient, or both.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see. e.g., NCBI web site ncbi.nlm.nih.gov/BLAST or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. The biomarkers described herein can be detected with probes that have, e.g., more than 70% identity over a specified region, or for example, more than 80%, 85%, 90%, 95%, 96%, 97%, 98%, or 99% identity to the reference sequence provided by the accession number, up to 100% identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman. Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP. BESTFIT. FASTA, and TFASTA in the Wisconsin Genetics Software Package, Genetics Computer Group, 575 Science Dr., Madison, Wis.), or by manual alignment and visual inspection (see. e.g., Current Protocols in Molecular Biology (Ausubel et al., eds. 1987-2005. Wiley Interscience)).

One example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word-length (W) of 11, an expectation (E) of 10, M=5, N=−4 and a comparison of both strands. For amino acid sequences, the BLASTP program uses as defaults a word-length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5. N=−4, and a comparison of both strands.

"Nucleic acid" refers to deoxyribonucleotides or ribonucleotides and polymers thereof in either single- or double-stranded form, or complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985): Rossolini et al., Mol. Cell. Probes 8:91-98 (1994)). The term nucleic acid is used interchangeably with gene, cDNA. mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline. γ-carboxyglutamate, and O-phosphoserine Amino acid analogs refers to compounds that have the same basic chemical structure as a naturally occurring amino acid, i.e., an .alpha. carbon that is bound to a hydrogen, a carboxyl group, an amino group, and an R group. e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

As an example, the following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S). Threonine (T); and 8) Cysteine (C), Methionine (M). See. e.g., Creighton. Proteins (1984).

The phrase "stringent hybridization conditions" refers to conditions under which a probe will hybridize to its target subsequence, typically in a complex mixture of nucleic acids, but no other sequences. Stringent conditions are sequence-dependent and will be different in different circumstances. Longer sequences hybridize specifically at higher temperatures. An extensive guide to the hybridization of nucleic acids is found in Tijssen. Techniques in Biochemistry and Molecular Biology—Hybridization with Nucleic Probes, "Overview of principles of hybridization and the strategy of nucleic acid assays" (1993). Generally, stringent conditions are selected to be about 5-10.degree. C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical although high stringency annealing temperatures can range from about 50° C. to about 65° C., depending on the primer length and specificity. Typical cycle conditions for both high and low stringency amplifications include a denaturation phase of 90° C.-95° C. for 30 seconds to 2 min., an annealing phase lasting 30 seconds to 2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes. IgG. IgM. IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An example of an immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to V.sub.H-C.sub.H1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, such as over a region of at least about 20, 25, 30, 35, 40, 45, 50, 75, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, such as greater than about 96%, 97%, 98%, 99%, or higher nucleotide sequence identity, for example over a region of at least about 20, 25, 30, 35, 40, 45, 50, 75, 100, 200, 500, 1000, or more nucleotides, to a reference nucleic acid sequence. A polynucleotide or polypeptide sequence is typically from a mammal including, but not limited to, primate, e.g., human: rodent, e.g., rat, mouse, hamster; cow, pig, horse, sheep, or any mammal. The nucleic acids and proteins of the invention include both naturally occurring and/or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see. e.g., Harlow & Lane, Antibodies. A Laboratory Manual (1988) for a description of immunoassay formats and conditions that can be used to determine specific immunoreactivity).

"Inhibitors," "activators." and "modulators" of the markers are used to refer to activating, inhibitory, or modulating molecules identified using in vitro and in vivo assays of endometrial cancer biomarkers. Inhibitors are compounds that, e.g., bind to, partially or totally block activity, decrease, prevent, delay activation, inactivate, desensitize, or down regulate the activity or expression of endometrial cancer biomarkers. "Activators" are compounds that increase, open, activate, facilitate, enhance activation, sensitize, agonize, or up regulate activity of endometrial cancer biomarkers, e.g., agonists. Inhibitors, activators, or modulators also include genetically modified versions of endometrial cancer biomarkers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like. Such assays for inhibitors and activators include, e.g., expressing endometrial cancer biomarkers in vitro, in cells, or cell extracts, applying putative modulator compounds, and then determining the functional effects on activity, as described above.

Samples or assays comprising endometrial cancer biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of endometrial cancer biomarkers is achieved when the activity value relative to the control is about 80%, such as 50%, including 25-0%. Activation of endometrial cancer biomarkers is achieved when the activity value relative to the control (untreated with activators) is 110%, such as 150%, including 200-500% (i.e., two to five fold higher relative to the control), including 1000-3000% higher.

The term "biocompatible," as used herein, refers to a material that does not elicit a substantial detrimental response in the host.

As used herein, the term "biologically active fragments" or "bioactive fragment" of the polypeptides encompasses natural or synthetic portions of the full length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate endometrial cancer biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, such as less than about 2000 Daltons, including between about 100 to about 1000 Daltons, including between about 200 to about 500 Daltons.

The term "contacting" refers to the act of touching, making contact, or of bringing to immediate or close proximity, including at the cellular or molecular level, for example, to bring about a physiological reaction, a chemical reaction, or a physical change. e.g., in a solution, in a reaction mixture, in vitro, or in vivo.

Methods involving conventional molecular biology techniques are described herein. Such techniques are generally known in the art and are described in detail in methodology treatises, such as Molecular Cloning: A Laboratory Manual. 2nd ed., vol. 1-3, ed. Sambrook et al., Cold Spring Harbor Laboratory Press. Cold Spring Harbor. N.Y., 1989: and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22: 1859-1862, 1981, and Matteucci et al., J. Am. Chem. Soc. 103:3185, 1981.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

Such assays are coupled with processes or systems to store and process information and to help quantify levels, signals, etc. and to digitize the information for use in comparing levels.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

"Plurality" means at least two.

The term "prevent," as used herein, means to stop something from happening, or taking advance measures against something possible or probable from happening. In the context of medicine. "prevention" generally refers to action taken to decrease the chance of getting a disease or condition.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "subject" of analysis, diagnosis, or treatment is an animal. Such animals include mammals, preferably a human.

The terms "comprises." "comprising," and the like can have the meaning ascribed to them in U.S. Patent Law and can mean "includes," "including" and the like. As used herein, "including" or "includes" or the like means including, without limitation.

Biomarker for Endometrial Cancer Recurrence—USP14

```
                                          (SEQ ID NO: 1)
MPLYSVTVKWGKEKFEGVELNTDEPPMVKFAQLFALTGVQPARQKVMVK

GGTLKDDDWGNIKIKNGMTLLMMGSADALPEEPSAKTVFVEDMTEEQLA

SAMELPCGLTNLGNTCYMNATVQCIRSVPELKDALKRYAGALRASGEMA

SAQYITAALRDLFDSMDKTSSSIPPIILLQFLHMAFPQFAEKGEQGQYL

QQDANECWIQMMRVLQQKLEAIEDDSVKETDSSSASAATPSKKKSLIDQ

FFGVEFETTMKCTESEEEEVTKGKENQLQLSCFINQEVKYLFTGLKLRL

QEEITKQSPLTQRNALYIKSSKISRLPAYLTIQMVRFFYKEKESVNAKV

LKDVKFPLMLDMYELCTPELQEKMVSFRSKFKDLEDKKVNQQPNTSDKK

SSPQKEVKYEPFSFADDIGSNNCGYYDLQAVLTHQGRSSSSGHYVSWVK

RKQDEWIKFDDDKVSIVTPEDILRLSGGGDWHIAYVLLYGPRRVEIMEE

ESEQ
```

Accession numbers for human mRNA are NM_005151 and NM_001037334; Accession numbers for human protein are NP_001032411 and NP_005142 (all of which are incorporated herein by reference).

The linkage of a diagnostic biomarker to a specific therapy results in the "intelligent" treatment of cancer by identifying subjects whose disease will respond to a specific treatment. This is often referred to as "individualized therapy" or "personalized medicine."

The deubiquitinating enzyme USP14 is a component of the ubiquitin-proteasome-degradation system. Deubiquitinating enzymes act as master regulators in a number of metabolic processes including cell growth, differentiation, and apoptosis. Deubiquitinating enzymes have been shown to be differentially expressed and activated in a number of cancer settings. Their aberrant activity has been linked to cancer progression, initiation and onset of chemoresistance and their inhibition can serve as a potential therapeutic target.

The Ubiquitin-Specific Protease 14 (USP14) is a proteasome-associated deubiquitinating enzyme responsible for cleaving ubiquitin chains from proteins destined for proteasome degradation. Aberrant expression of USP14 has been implicated in a variety of cancers, including multiple myeloma, colorectal cancer, lung cancer, and epithelial ovarian cancer [10-14]. Aberrant expression of USP14 in epithelial ovarian cancer has been associated with poor prognosis [12]. Furthermore, pharmacological inhibition of USP14 with the FDA approved small-molecule inhibitor VLX1570 has been suggested as an alternative treatment method for cancer treatment in a number of cancer settings, including breast and ovarian cancer [15, 16].

To date, the role of USP14 as a biomarker and molecular target in the endometrial cancer setting is largely unknown. Herein it is shown that expression of USP14 is an independent predictor for recurrence in a retrospective cohort of women with stage I endometrial adenocarcinoma. Specifically the data indicate that after taking into account other known risk factors for recurrence, namely disease grade, stage, receipt of adjuvant therapy and presence of lymphovascular space invasion. USP14 can be used as a biomarker to stratify endometrial cancer patients according to risk of recurrence. Furthermore, it is shown that pharmacological inhibition of USP14 severely affects the viability of carboplatin resistant endometrial cancer cells with a mechanism consistent with arrest of the cells in the G2/M phase of the cell cycle followed by caspase-3 mediated onset of apoptosis. In light of these findings, USP14 is a novel biomarker of recurrence in endometrial cancer, as well as a molecular target for its treatment.

Herein it is shown for the first time that USP14 can be used as a biomarker to stratify endometrial cancer patients by risk of recurrence. Further, the ubiquitin-proteasome system is aberrantly expressed in highly proliferating, Ki67 positive, endometrial cancer cells in situ. Finally, pharmacological targeting of USP14 decreases the viability of chemotherapy resistant endometrial cancer cells with a mechanism that is consistent with UPS stress followed by onset of apoptosis-mediated cell death.

Diagnostic Methods

The present invention provides methods of diagnosing recurrence of endometrial cancer in a patient with endometrial cancer by detecting the expression of markers differentially expressed in cells from a patient with endometrial cancer. Diagnosis involves determining the level of a biomarker polynucleotide or the corresponding polypeptide in a patient or patient sample and then comparing the level to a baseline or range. Typically, the baseline value is representative of levels of the polynucleotide or nucleic acid/polypeptide in a healthy person not suffering from, or destined to develop, recurring endometrial cancer, as measured using a biological sample such as an endometrial biopsy or a sample of a bodily fluid. Variation of levels of a polynucleotide or corresponding polypeptide of the invention from the baseline range (either up or down) indicates that the patient has an increased risk of developing recurring endometrial cancer. Markers useful in these diagnoses include, but are not limited to, USP14.

As used herein, the term "diagnosis" refers to distinguishing between having and not having recurring endometrial cancer.

Antibody reagents can be used in assays to detect expression levels of the biomarkers of the invention in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (ETA) such as enzyme multiplied immunoassay technique (EMIT), enzyme-linked immunosorbent assay (ELISA), IgM antibody capture ELISA (MAC ELISA), and microparticle enzyme immunoassay (META); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods. 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, C A: Kit #449430) and can be performed using a Behring Nephelometer Analyzer (Fink et al., J. Clin. Chem. Clin. Biochem, 27:261-276 (1989)).

Specific immunological binding of the antibody to the target can be detected directly or indirectly. Direct labels include fluorescent or luminescent tags, metals, dyes, radionuclides, and the like, attached to the antibody. An antibody labeled with iodine-125 can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin. R-phycoerythrin, rhodamine. Texas red, and lissamine Indirect labels include various enzymes well known in the art, such as horseradish peroxidase (HRP), alkaline phosphatase (AP), .beta.-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a .beta.-galactosidase detection system can be used with the chromogenic substrate o-nitrophenyl-.beta.-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Alternatively, nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al. General nucleic acid hybridization methods are described in Anderson, "Nucleic Acid Hybridization," BIOS Scientific Publishers, 1999. Amplification or hybridization of a plurality of nucleic acid sequences (e.g., genomic DNA. mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing. Sanger sequencing, capillary array DNA sequencing, thermal cycle sequencing (Sears et al., Biotechniques, 13:626-633 (1992)), solid-phase sequencing (Zimmerman et al., Methods Mol. Cell Biol., 3:39-42 (1992)), sequencing with mass spectrometry such as matrix-assisted laser desorption/ionization time-of-flight mass spectrometry (MALDI-TOF/MS; Fu et al., Nat. Biotechnol., 16:381-384 (1998)), and sequencing by hybridization. (Chee et al., Science, 274:610-614 (1996); Drmanac et al., Science, 260:1649-1652 (1993); Drmanac et al., Nat. Biotechnol., 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine. Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by endometrial cancer biomarkers, such as antibodies, may be labeled using an appropriate marker, such as a fluorescent marker.

The above tests can be carried out on samples derived from patients' bodily fluids and tissue extracts/sections (homogenates or solubilized tissue) such as from tissue biopsy and autopsy material. Levels of USP14, determined in cells and tissues from a patient suspected of suffering from endometrial cancer by measuring the polypeptide or by transcription levels, are compared to levels of USP14 in normal or control cells or tissues (e.g., those without endometrial cancer or recurring endometrial cancer). Elevated levels of USP14 measured in the patient as compared to levels in the same cells, tissues, or bodily fluids obtained from normal, healthy individuals are indicative of endometrial cancer. By "elevated levels" it is meant an increase in measured USP14 levels in a patient as compared to USP14 levels in the same normal cells or tissues. Detection of elevated USP14 levels is useful in the diagnosis of recurring endometrial cancer.

Levels of USP14 are advantageously compared to controls according invention. The control maybe a predetermined value, which can take a variety of forms. It can be a single cutoff value, such as a median or mean. It can be established based upon comparative groups, such as in groups not having elevated unopposed estrogen levels and groups having elevated unopposed estrogen levels. Another example of comparative groups would be groups having a particular disease, condition or symptoms and groups without the disease, condition or symptoms such as a group with endometrial pre-malignancy or endometrial cancer and a group without endometrial pre-malignancy or endometrial cancer. Another comparative group would be a group with a family history of a condition such as endometrial cancer and a group without such a family history.

Compositions and Kits

The invention provides compositions and kits for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies.

As used herein, an "instructional material" includes a publication, a recording, a diagram, or any other medium of expression which can be used to communicate the usefulness of the invention in the kit diagnosing or treating. The instructional material of the kit of the invention may, for example, be affixed to a container which contains the identified invention, or portion thereof, or be shipped together with a container which contains the invention or portion thereof. Alternatively, the instructional material may be shipped separately from the container with the intention that the instructional material and the compound be used cooperatively by the recipient.

The invention also includes kits comprising the USP14 binding agents described herein. The kit includes a package housing a container that contains an agent for determining the level of USP14 in a sample. The kit may also include a control. The kit may also include instructions as described herein. The instructions typically will be in written form and will provide guidance for carrying out the assay embodied by the kit and for making a determination based upon that assay.

Methods to Identify Compounds/Screening

A variety of methods may be used to identify compounds that treat endometrial cancer. Typically, an assay that provides a readily measured parameter is adapted to be performed in the wells of multi-well plates in order to facilitate the screening of members of a library of test compounds as described herein. Thus, in one embodiment, an appropriate number of cells can be plated into the cells of a multi-well plate, and the effect of a test compound on the expression of a biomarker can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.). Aldrich (St. Louis, Mo.). Sigma-Aldrich (St. Louis. Mo.), Fluka Chemika-Biochemica Analytika (Buchs Switzerland) and the like.

In one embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the expression of the biomarkers of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka. Int. J. Pept. Prot. Res., 37:487-493 (1991) and Houghton et al., Nature, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., PNAS USA, 90:6909-6913 (1993)), vinylogous polypeptides (Hagihara et al., J. Amer. Chem. Soc., 114:6568 (1992)), nonpeptidal peptidomimetics with glucose scaffolding (Hirschmann et al., J. Amer. Chem. Soc., 114:9217-9218 (1992)), analogous organic syntheses of small compound libraries (Chen et al., J. Amer. Chem. Soc., 116:2661 (1994)), oligocarbamates (Cho et al., Science. 261:1303 (1993)), and/or peptidyl phosphonates (Campbell et al., J. Org. Chem., 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see. e.g., Liang et al., Science, 274: 1520-1522 (1996) and U.S. Pat. No. 5,593,853), small organic molecule libraries (see. e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds. U.S. Pat. No. 5,506, 337; benzodiazepines. U.S. Pat. No. 5,288,514, and the like).

Devices for the preparation of combinatorial libraries are commercially available (see, e.g., 357 MPS, 390 MPS. Advanced Chem Tech, Louisville Ky., Symphony, Rainin, Woburn, Mass., 433A Applied Biosystems, Foster City, Calif., 9050 Plus, Millipore, Bedford. Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd. Moscow, RU, 3D Pharmaceuticals, Exton, Pa., Martek Biosciences. Columbia, Md., etc.)

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds is possible using the integrated systems of the invention.

Methods to Inhibit Marker Protein Expression/Methods to Treat

A variety of nucleic acids, such as antisense nucleic acids, siRNAs, microRNAs, or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 including each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which auto-catalytically cleaves the target sense mRNA.

With regard to antisense, siRNA, microRNAs, or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered, 2'-O-propyl and 2'-methoxyethoxy ribose modifications stabilize oligonucleotides to nucleases in cell culture and in vivo.

"RNAi molecule" or a "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, a siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent. Roche, Alameda, Calif.; Lipofectamine formulations, Invitrogen, Carlsbad. Calif.). Delivery mediated by cationic liposomes, by retroviral vectors and direct delivery are efficient. Another possible delivery mode is targeting using antibodies to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., Curr Drug Delivery (2006) 3:147-5 and Patil, et al., AAPS Journal (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bio-adhesive microspheres, or by proteinaceous vectors (O'Hare and Normand, International PCT Publication No. WO 00/53722).

In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, microRNAs, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison. Wis.; Invitrogen, Carlsbad, Calif.; InvivoGen, San Diego, Calif.; and Imgenex, San Diego. Calif. Typically, expression vectors for transcribing siRNA molecules will have a U6 promoter.

In some embodiments, antisense, siRNA, microRNAs, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen. Carlsbad, Calif.; Open BioSystems. Huntsville. Ala.; and Imgenex. San Diego, Calif.

Further, a variety of proteins, such as antibodies against the marker, may be used to inhibit the function of the markers of this invention.

In addition, or as a solo treatment, other, treatments may be used to treat the cancer, such as chemotherapy and radiation.

In accordance with one embodiment, a method of treating a subject in need of such treatment is provided. The method comprises administering a pharmaceutical composition comprising at least one compound of the present invention to a subject in need thereof.

Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents: buffers: salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences. Mack Publishing Co., Easton, Pa., which is incorporated herein by reference.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. For example, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

A variety of vaginal drug delivery systems is known in the art. Suitable systems include creams, foams, tablets, gels, liquid dosage forms, suppositories, and pessaries. Mucoadhesive gels and hydrogels, comprising weakly crosslinked polymers which are able to swell in contact with water and spread onto the surface of the mucosa, have been used for vaccination with peptides and proteins through the vaginal route previously. The present invention further provides for the use of microspheres for the vaginal delivery of peptide and protein drugs. More detailed specifications of vaginally administered dosage forms including excipients and actual methods of preparing said dosage forms are known, or will be apparent, to those skilled in this art. For example, Remington's Pharmaceutical Sciences (15th ed., Mack Publishing, Easton, Pa., 1980) is referred to.

The following examples are intended to further illustrate certain embodiments of the invention and are not intended to limit the scope of the invention in any way.

EXAMPLE

Example 1—USP14 is a Predictor of Recurrence in Endometrial Cancer and a Molecular Target for Endometrial Cancer Treatment Introduction Endometrial adenocarcinoma is the most common gynecologic malignancy in the United States with an estimated nearly 55,000 new cases 2015 [1]. A majority of patients are diagnosed at an early stage with an overall favorable prognosis, although approximately 20% will die from the disease [1, 2]. Clinical factors such as grade, histologic characteristics and surgical stage are important determinants of prognosis for endometrial adenocarcinoma. Among women with early stage and low grade endometrial cancer, identified as low and low intermediate risk groups and representing 60% of endometrial cancers, overall survival is greater than 93% and adjuvant therapy beyond surgical hysterectomy offers no survival benefit [3-5]. A major and continued challenge in endometrial cancer management is the development of targeted therapy for those with early stage endometrial cancer at higher risk of recurrence and de-escalation of management for those at lower risk.

The current risk stratification system relies heavily on histologic features, classifying women with endometrial adenocarcinoma into two groups, Type I or Type II [6]. Type I endometrial adenocarcinomas, the most common subtype, typically occur in the setting of excessive estrogen and consist of low grade endometrioid, hormone receptor positive cancers with good prognosis. Type II endometrial adenocarcinomas include non-endometrioid, high grade, TP53-mutated, hormone-receptor negative cancer and are associated with poor prognosis [7, 8]. Unfortunately, these risk groups fail to predict recurrence in some women as 15% of women with endometrioid endometrial cancer (Type 1) will experience recurrence and risk stratification based on histology or grade alone may fail to capture this subset of women [3, 9]. Therefore Molecular Markers, Such as USP14, are Needed to Facilitate Risk Stratification and treatment of early stage endometrial cancer.

Materials and Methods

Patient Samples

Approval for this study was granted by the University of Minnesota Institutional Review Board. Patients diagnosed with endometrial adenocarcinoma between January 2000 and July 2012 were identified by querying the gynecologic cancer database at the University of Minnesota. Inclusion criteria were as follows: 1) surgical staging including total hysterectomy and bilateral salpingo-oophorectomy with or without pelvic and periaortic lymph node dissection and omentectomy; 2) histologically confirmed endometrial adenocarcinoma; 3) confirmed stage I disease, retrospectively determined according to the FIGO 2009 criteria [34]: and 4) minimum of 36 months follow-up. Patient demographic and clinical data were extracted from the electronic medical record, including age at diagnosis, race, body mass index, parity, menopausal status, medical comorbidities, disease stage, adjuvant therapy received, and dates of recurrence and death. The pathologic diagnosis was confirmed in each case by a board-certified pathologist. Histologic characteristics including tumor grade, histologic subtype, lymphovascular space invasion, maximum myometrial invasion, and other pathologic characteristics were also recorded.

A total of 203 patients diagnosed with stage I endometrial adenocarcinoma met the inclusion criteria. Of those, a representative sample of 107 were selected for staining with an antibody for USP14, oversampling those who experienced a recurrence. A representative block of tumor was selected from each case by the pathologist. A five micron thick unstained section was cut from each block and mounted onto a glass slide. The unstained slides were subjected to immunohistochemistry against USP14 and Ki67.

Immunohistochemistry for USP14 and Ki67

Five-micron thick formalin-fixed, paraffin-embedded sections were deparaffinized and rehydrated by sequential washing with xylene, 100% ethanol, 95% ethanol, 80% ethanol, and PBS. For antigen retrieval, slides were immersed in Reveal Decloaker (Biocare Medical, Concord, Calif.) and steamed for 30 min at 100° C. Endogenous peroxidase activity was blocked with 3% $H_2O_2$ for 10 min. After washing with PBS, slides were blocked with 10% normal goat serum in PBS for 10 min at room temperature, followed by incubation with rabbit anti-human polyclonal USP14 antibody (Bethyl Laboratories; /USP14 Antibody. A300-920A; immunogen between 450 and c-term) at a concentration of 1:750 in blocking solution overnight at 4° C. After washing twice with PBS, slides were incubated with a biotinylated anti-rabbit secondary antibody conjugated (10 min) and streptavidin/horseradish peroxidase (10 min; Dako), followed by 3,3-diaminobenzidine (Phoenix Biotechnologies) substrate for 3 min. Slides were lightly counterstained with Gill No. 3 hematoxylin (Sigma) for 60 s, dehydrated, and cover-slipped.

All of the USP14 immunostained slides were reviewed by two independent pathologists in addition to a panel of five basic scientists, all of whom were blinded to the clinical outcome of the corresponding patients. The staining intensity was rated as follows: 0=no staining, 1+=weak intensity, 2+=moderate intensity, and 3+=high intensity.

A subset of patients (n=31) were additionally stained for Ki67 using the same procedure as described above with the substitution of the Ki-67 monoclonal mouse antibody MIB-1 (Dako, Carpinteria, Calif.) as the primary antibody at a concentration of 1:150. The correlation between USP14 and Ki67 was evaluated by two independent researchers. Blind to the Ki67 staining, each researcher chose one field each per patient that represented low and high intensity USP14 staining areas, respectively. They then identified the corresponding area of Ki67 staining and counted the number of Ki67 stained cells in one high power field (40×) in the areas corresponding to USP14 weak (blue window/cold) and strong (red window/hot) intensity.

Chemicals

The USP14 inhibitor VLX1570 was synthetized as previously described [22]. The 2,3-bis[2-methoxy-4-nitro-5-sulfophenyl]-2H-tetrazolium-5-carboxanilide inner salt (WST-1) was purchased from Cayman Chemicals. Propidium iodide was purchased from Sigma.

Cell Lines

The endometrial cancer cell lines were obtained as follows: ECC-1 (American Type Culture Collection); EFE-184 (German Tissue Repository DSMZ); HEC-155 (Japanese Health Science Research Bank). Cell lines were cultured in DMEM supplemented with 10% fetal bovine serum, 100 IU/mL penicillin, and 100 μg/mL streptomycin at 5% $CO_2$.

Cell Viability Assay

Cell viability was determined by 2,3-bis[2-methoxy-4-nitro-5-sulfophenyl]-2H-tetrazolium-5-carboxanilide inner salt assay as previously described [35, 36]. Briefly, cells were seeded at the concentration of 1.000 per well in 100 μL medium in 96-well plate and treated with the indicated concentrations of drugs. At the indicated time points, cells were incubated according to the manufacturer's protocol with the WST-1 labeling mixture for 2 hours. Formazan dye was quantified using a spectrophotometric plate reader to measure the absorbance at 450 nm (ELISA reader 190; Molecular Devices).

Antibodies and Western Blot Analysis

Total cellular protein (10-20 μg) from each sample was separated by SDS-PAGE, transferred to PVDF membranes and subjected to Western blot analysis. Antibodies for Western blot analysis were obtained by the following commercial sources: anti-USP14 (Bethyl Laboratories), anti-ubiquitin (Santa Cruz Biotechnology), anti-β-actin (Sigma). Peroxidase-linked anti-mouse Immunoglobulin G and peroxidase-linked anti-rabbit Immunoglobulin G were from Amersham.

Antibodies and Flow Cytometry

Cell cycle status following treatment with drug or vehicle alone was determined via flow cytometry analysis. Specifically, cells were harvested at indicated time points and fixed in 70% ethanol on ice for 2 hours. Following washing with PBS, cells were stained with 0.1% (m/v) propidium iodide in PBS-T. Apoptosis was measured using antibodies against active Caspase-3 (BD Pharmingen) or Annexin V (BD Pharmingen) which were combined with propidium iodide staining (Sigma-Aldrich). For apoptosis assays, samples were fixed and stained according to manufacturer's instructions. Fluorescence was measured with a FACSCantoII flow cytometer (Becton Dickinson) and analyzed with FlowJo software.

Statistical Analysis

The goal of the analysis was to determine the association between USP14 staining intensity and recurrence of endometrial adenocarcinoma within 36 months of diagnosis among women with stage I disease. The mean USP14 straining level of the three values (two pathologists and panel of scientists) was calculated for each patient and used for analyses. Available patient demographic and clinical data were summarized and compared by recurrence status using Chi-squared and Fisher's Exact tests. Similarly, USP14 staining intensities were compared across demographic and clinical variables to identify potential confounding factors. A multivariate logistic regression model was conducted to determine the additional utility of USP14 staining intensity as a predictor of recurrence, given knowledge of other risk factors including age, obesity, histology (endometrioid/other), highest pathology grade, disease stage (IA/IB), lymphovascular space invasion (yes/no) and adjuvant therapy received (yes/no). Due to the small sample size, the final multivariate model was selected using backwards selection, keeping variables with $p<0.10$. To explore the predictive value of USP14 in the pre-operative setting, a receiver operating characteristic (ROC) analysis was conducted, comparing the addition of USP14 to grade as compared to grade alone. The area under the ROC curve (AUC) estimates and 95% confidence interval are presented and were compared [37]. Finally, the difference in the number of USP14 stained cells between the strong and weak Ki67 areas, using the mean value of the two researchers, was analyzed using the Wilcoxon Signed Rank Test. All analyses were conducted using SAS version 9.3 (Cary, N.C.) and p-values<0.05 were considered statistically significant.

Results

Overexpression of USP14 is Associated with Recurrence in Endometrial Cancer.

Measures of disease aggressiveness (stage, histology, and myometrial invasion) are known to be related to recurrence among women with stage I endometrial cancer, however a subset of patients with anticipated good prognostic factors will recur. It was determined herein whether USP14 expression level could serve as an independent marker of recurrence. To that end, the association between USP14 and recurrence in women with endometrial adenocarcinoma was evaluated using a retrospective cohort of stage I endometrial adenocarcinoma cases treated at our institution. A total of 107 patients with at least 36 months of follow-up, oversampling those who recurred, were included in the analysis.

Patients were on average 60.6±9.6 years old at diagnosis, most were white, obese, menopausal, and hypertensive. The relationships between numerous demographic and clinical variables and recurrence within 36 months of diagnosis were explored to both describe the population and identify potential confounding factors. As expected, numerous clinical factors were statistically significantly associated with recurrence in this population, including disease stage IB, myometrial invasion>50%, tumor size>2 cm, and presence of lymphovascular space invasion (Table 1).

TABLE 1

Factors associated with endometrial adenocarcinoma recurrence within 36 months.

| | Did Not Recur (N = 88) | | Recurred (N = 19) | | |
|---|---|---|---|---|---|
| | N | % | N | % | p-value |
| Age at Diagnosis | | | | | 0.92 |
| <50 years | 9 | 10.2 | 1 | 5.3 | |
| 50-69 years | 66 | 75.0 | 15 | 79.0 | |
| 70+ years | 13 | 14.8 | 3 | 15.8 | |
| Race | | | | | 0.42 |
| Black | 4 | 4.6 | 0 | 0.0 | |
| White | 72 | 81.8 | 19 | 100.0 | |
| Other | 8 | 4.6 | 0 | 0.0 | |
| Unknown/Declined | 4 | 9.1 | 0 | 0.0 | |
| Obese | | | | | 0.79 |
| No | 28 | 32.6 | 5 | 26.3 | |
| Yes | 58 | 67.4 | 14 | 73.7 | |
| Nulliparous | | | | | 0.35 |
| No | 59 | 73.8 | 13 | 86.7 | |
| Yes | 21 | 26.3 | 2 | 13.3 | |
| Menopausal | | | | | 0.73 |
| No | 15 | 17.4 | 2 | 11.1 | |
| Yes | 71 | 82.6 | 16 | 88.9 | |
| Hypertension | | | | | 0.71 |
| No | 33 | 37.5 | 8 | 42.1 | |
| Yes | 55 | 62.5 | 11 | 57.9 | |
| Diabetes | | | | | 0.96 |
| No | 69 | 78.4 | 15 | 79.0 | |
| Yes | 19 | 21.6 | 4 | 21.1 | |
| Histology | | | | | 0.31 |
| Endometrioid | 75 | 85.2 | 14 | 73.7 | |
| Other | 13 | 14.8 | 5 | 26.3 | |
| Squamous Component | | | | | 0.90 |
| No | 56 | 65.1 | 12 | 66.7 | |
| Yes | 30 | 34.9 | 6 | 33.3 | |
| Highest Grade | | | | | 0.11 |
| 1 | 36 | 40.9 | 4 | 21.1 | |
| 2 | 30 | 34.1 | 6 | 31.6 | |
| 3 | 22 | 25.0 | 9 | 47.4 | |
| Disease Stage | | | | | <0.0001 |
| IA | 75 | 85.2 | 8 | 42.1 | |
| IB | 13 | 14.8 | 11 | 57.9 | |

TABLE 1-continued

Factors associated with endometrial adenocarcinoma recurrence within 36 months.

|  | Did Not Recur (N = 88) | | Recurred (N = 19) | | |
| --- | --- | --- | --- | --- | --- |
|  | N | % | N | % | p-value |
| Myometrial Invasion |  |  |  |  | 0.006 |
| None | 21 | 23.9 | 3 | 15.8 |  |
| <50% | 54 | 61.4 | 5 | 26.3 |  |
| ≥50% | 13 | 14.8 | 11 | 57.9 |  |
| Tumor Size |  |  |  |  | 0.07 |
| ≤2 cm | 24 | 28.2 | 1 | 5.6 |  |
| >2 cm | 61 | 71.8 | 17 | 94.4 |  |
| Lymphovascular Space Invasion |  |  |  |  | 0.008 |
| No | 73 | 84.9 | 11 | 57.9 |  |
| Yes | 13 | 15.1 | 8 | 42.1 |  |
| PPALND |  |  |  |  | 1.00 |
| No | 13 | 14.8 | 3 | 16.7 |  |
| Pelvic only | 5 | 5.7 | 1 | 5.6 |  |
| Yes - both | 70 | 79.6 | 14 | 77.8 |  |
| Received Adjuvant Therapy |  |  |  |  | 0.24 |
| No | 59 | 67.0 | 10 | 52.6 |  |
| Yes | 29 | 33.0 | 9 | 47.4 |  |

Figure 1B:
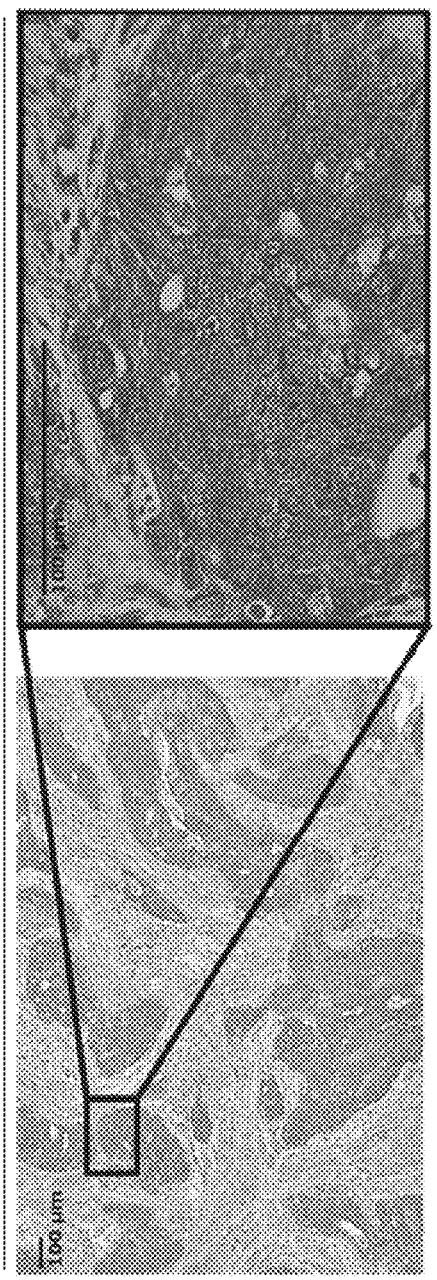
Figure 1C:
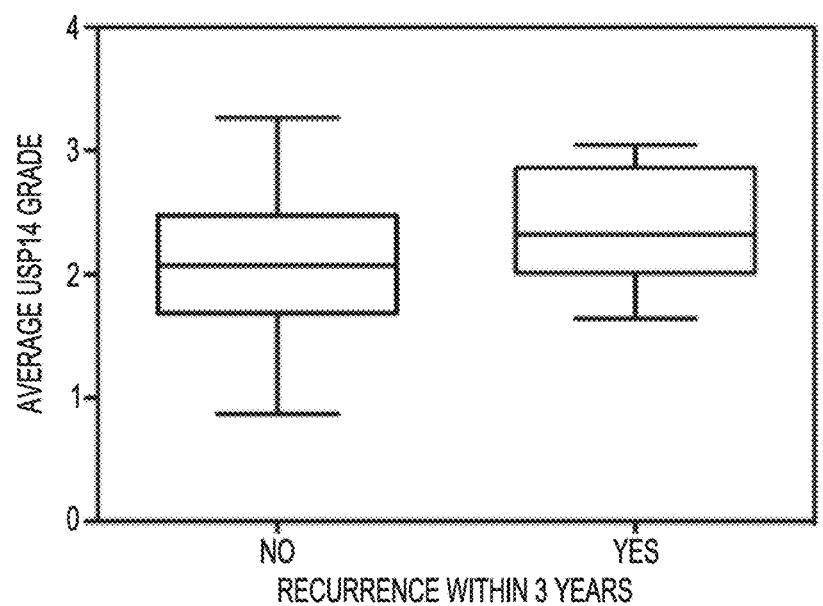

When comparing USP14 expression levels between patients who did and did not recur within 36 months, the median USP14 expression level was higher among the recurrent cases (FIG. 1; p=0.02). In order to address whether this association was independent of other risk factors of recurrence, a multivariate logistic regression model was constructed to adjust for highest grade, disease stage, lymphovascular space invasion, and receipt of adjuvant therapy. After adjustment, higher USP14 expression levels were highly associated with recurrence (odds ratio=6.6 [95% confidence interval: 1.5-28.7], p=0.01; Table 2).

TABLE 2

Multivariate logistic regression model of risk factors for recurrence within 36 months of diagnosis with stage I endometrial adenocarcinoma.

| Variable | Odds Ratio (95% CI) | p-value |
| --- | --- | --- |
| USP14 grade (per increase in USP14 staining grade) | 6.6 (1.5, 28.7) | 0.01 |
| Highest Grade |  | 0.05 |
| 1 | 1.0 |  |
| 2 | 1.3 (0.3, 6.2) |  |
| 3 | 7.4 (1.3, 44.1) |  |
| Stage |  | 0.01 |
| IA | 1.0 |  |
| IB | 6.0 (1.5, 24.3) |  |
| LVSI |  | 0.36 |
| No | 1.0 |  |
| Yes | 2.0 (0.5, 9.0) |  |
| Adjuvant Therapy |  | 0.43 |
| No | 1.0 |  |
| Yes | 0.6 (0.1, 2.3) |  |

Figure 2:
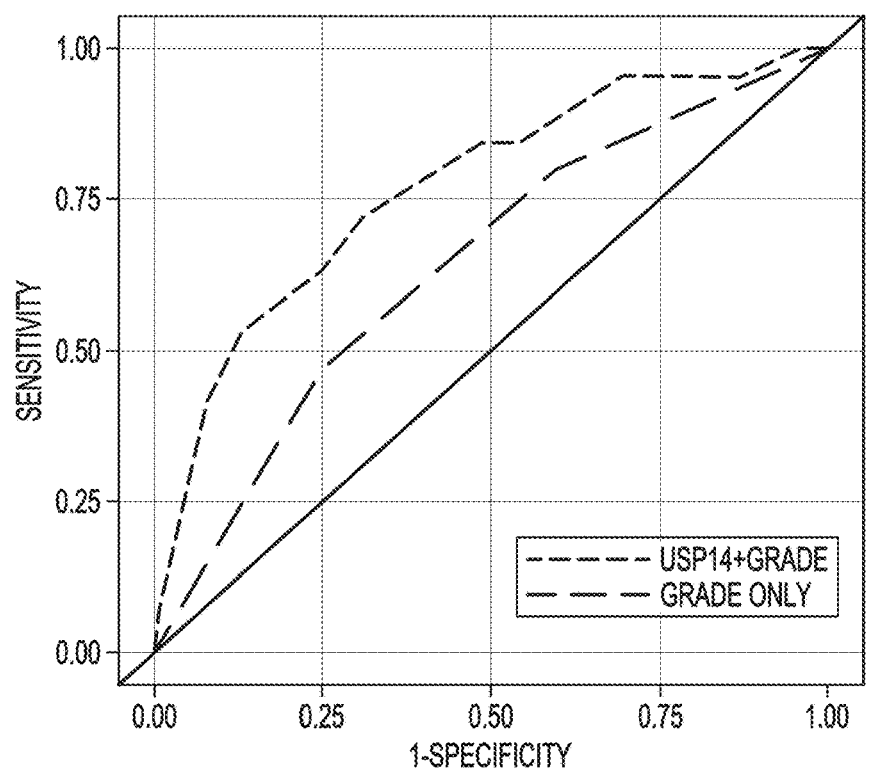
FIG. 2 shows USP14 staining intensity and grade are predictive of recurrence. Receiver operating characteristic (ROC) curves of grade only (black long dashed line) and USP14 staining intensity plus grade (gray short dashed line) indicating their ability to differentiate patients with endometrial adenocarcinoma by recurrence status. The solid diagonal line indicates no predictive value. Area under the curve estimates and 95% confidence intervals are 0.64 [95% CI: 0.51-0.77] and 0.77 [95% CI: 0.64-0.89], respectively (p=0.02).

To explore the potential clinical utility of USP14 expression levels in the pre-operative setting, the predictive ability of USP14 expression level, in addition to histologic grade, which is available via biopsy prior to surgery, was assessed. The combination of histologic grade and USP14 expression level was superior to grade alone in predicting recurrence, with area under the curve estimates and 95% confidence intervals of 0.77 [95% CI: 0.64-0.89] and 0.64 [95% CI: 0.51-0.77], respectively (p=0.02; FIG. 2).

USP14 is Aberrantly Expressed in Highly Proliferating Endometrial Cancer Cells In Situ.

Figure 3B:
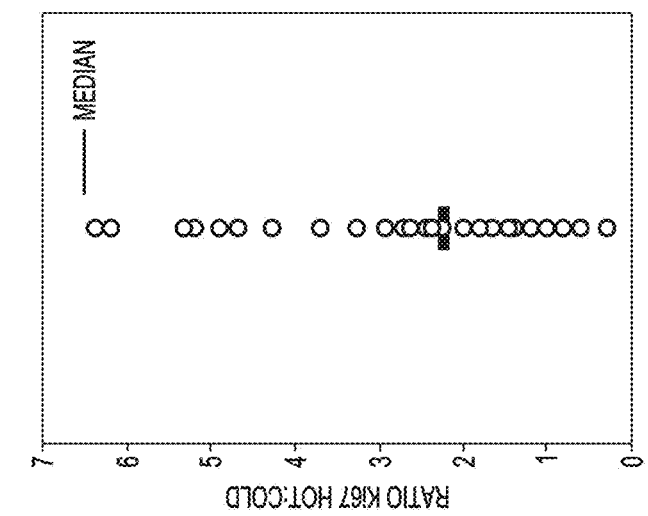
FIGS. 3A-B demonstrate that USP14 is overexpressed in proliferating endometrial cancer cells in situ. A, Immunohistochemical staining of USP14 and Ki67 in endometrial cancer tumors. Representative examples of strong (red window/hot) and weak (blue window/cold) USP14 (left panel) and Ki67 (right panel) staining intensity, respectively. B, Dot plot of the ratio of the number of Ki67 stained cells in areas with strong USP14 expression (hot) to areas with weak USP14 expression (cold) in 31 endometrial cancer tumor samples. Line=Median.
Figure 3A:
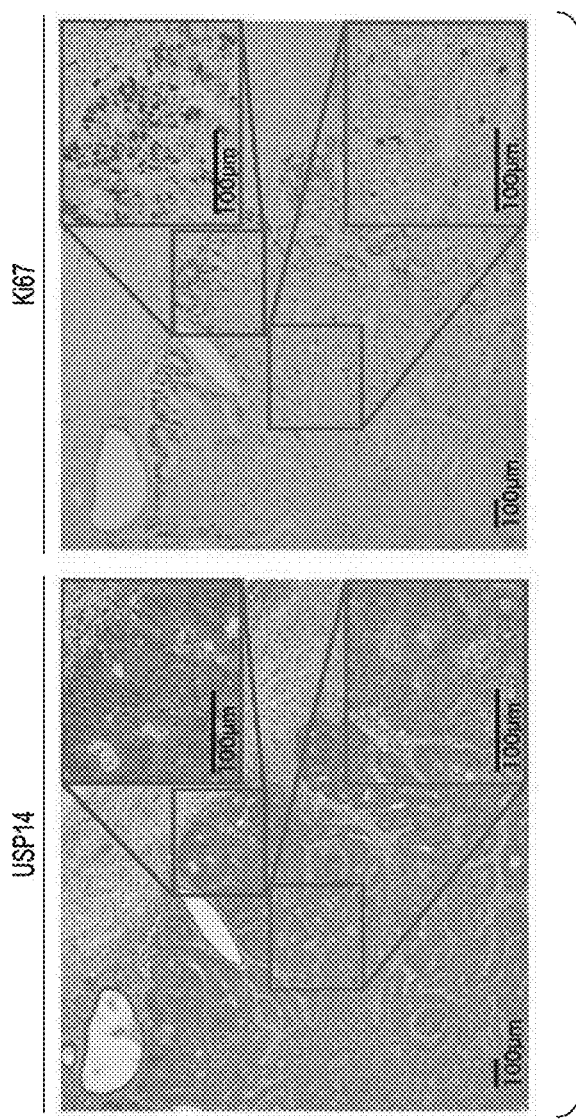

Uncontrolled proliferation is a characteristic of cancer and therefore is strongly associated with prognosis [17]. Ki67 is a marker of proliferation that has been used extensively in cancer research, particularly breast cancer, and has been shown to be associated with outcomes [18]. To examine whether USP14 expression levels were elevated among highly proliferative cells, we assessed the relationship between USP14 and Ki67 in a subset of 31 patient samples. Specifically, the number of Ki67 stained cells in corresponding areas of USP14 weak (low intensity) and strong (high intensity) fields for each patient were determined. There were more than twice as many Ki67 stained cells in the strong USP14 staining intensity areas than in the weak USP14 staining intensity areas (p<0.0001; FIG. 3). This suggests a correlation between tumor aggressiveness and USP14 activity.

Inhibition of USP14 Results in Decreased Cell Viability in Carboplatin Resistant Endometrial Cancer Cell Lines.

Figure 4A:
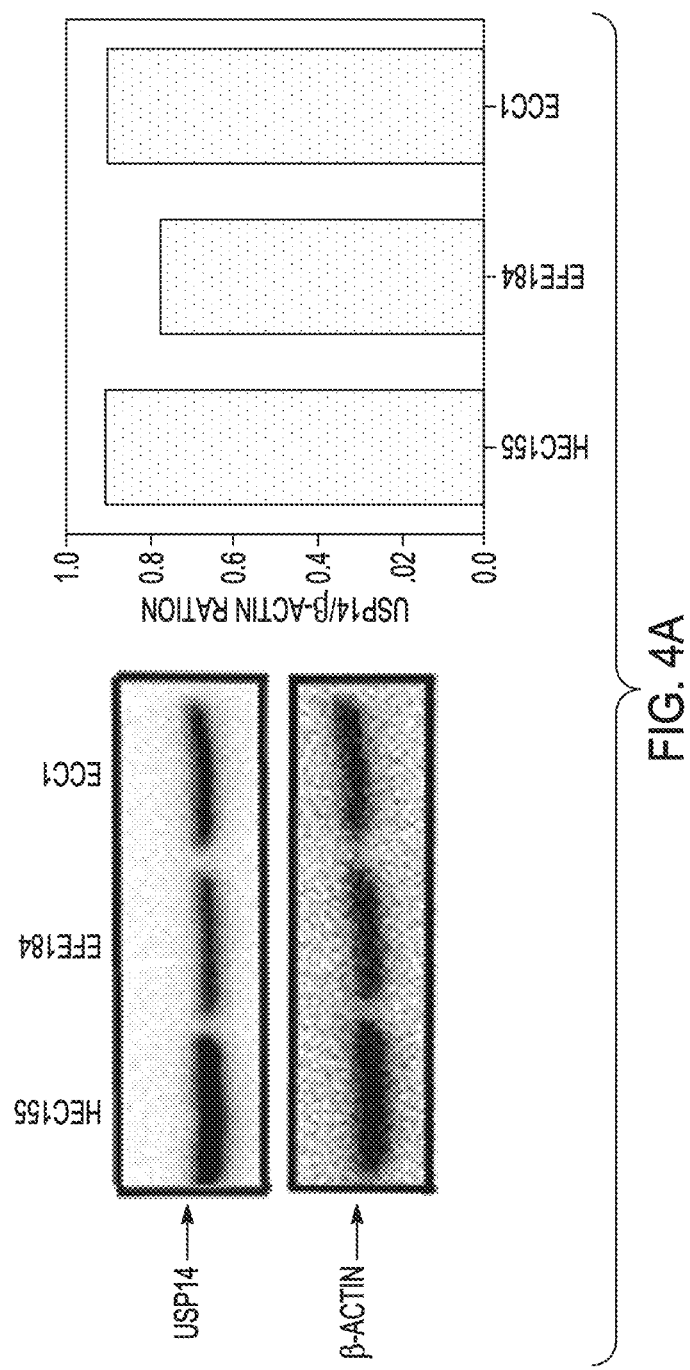
FIGS. 4A-C depict the effect of USP14 inhibition on carboplatin resistant endometrial cancer cells. A (left panel), Western blot analysis for USP14 expression levels in the endometrial cancer cell lines HEC155, EFE184 and ECC1. Equal protein loading in each line was verified using an antibody against β-actin. Right panel, quantification of USP14 expression in endometrial cancer cell lines expressed as USP14/β-actin ratio. B, dose-dependent inhibition of cell viability of HEC155 (left panel) and ECC1 (right panel) endometrial cancer cell lines exposed to increasing concentrations of VLX1570 over a period of 48 hours. Percentage of viable cells is relative to mock-treated controls. C, dose-dependent inhibition of cell viability of HEC155 (left panel) and ECC1 (right panel) endometrial cancer cell lines exposed to increasing concentrations of carboplatin over a period of 48 hours. Percentage of viable cells is relative to mock-treated controls.
Figure 4B:
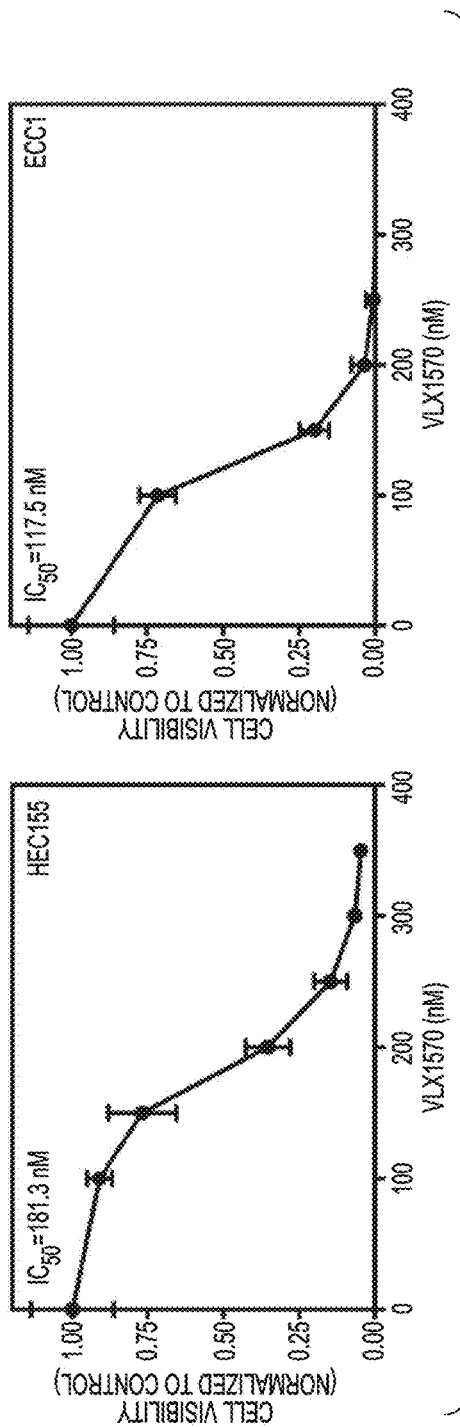
Figure 4B:
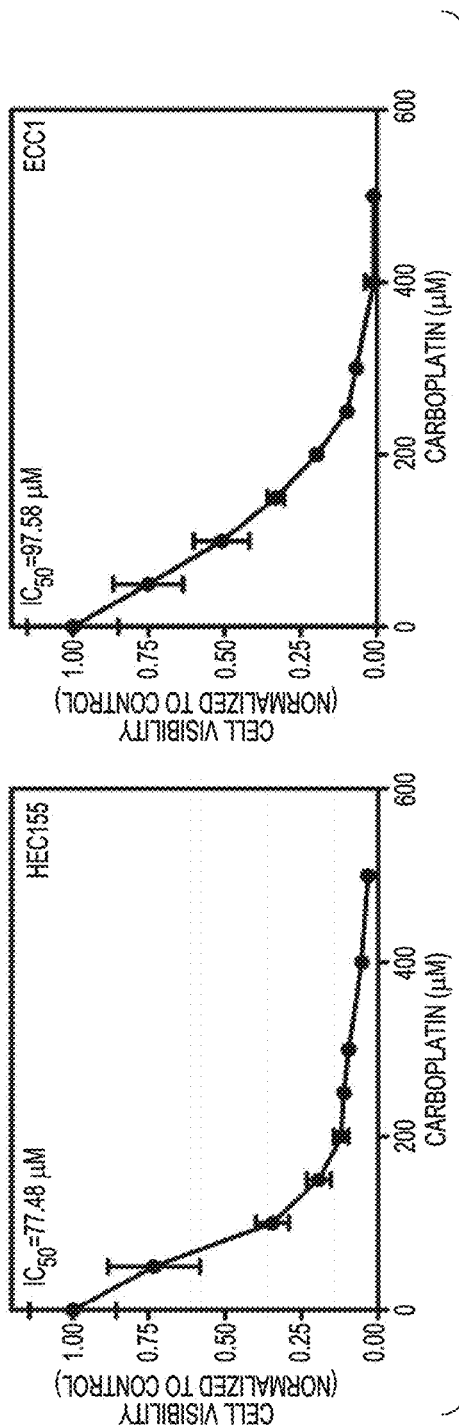

The correlation between USP14 expression levels and proliferation rate in endometrial cancer cells in situ suggests that aggressive endometrial cancer cells have a higher dependency upon USP14 activity. The next step was to investigate whether USP14 is a molecular target for endometrial cancer cells. To this end, the expression levels of USP14 in a panel of endometrial cancer cell lines including HEC155, EFE184 and ECC1 was first measured. These cells were chosen as they represent the most aggressive and most likely to recur endometrial cancer types [7, 19]. As shown in FIG. 4A (left panel), all cell lines tested expressed USP14 with HEC155 and ECC1 having the highest levels. Quantification of the USP14 expression levels expressed as ratio to β-actin is shown in FIG. 4A (right panel). Next, ECC1 and HEC155 endometrial cancer cells were exposed to increasing concentrations of the small-molecule inhibitor VLX1750 and the residual cell viability was measured after a period of 48 hours. As shown in FIG. 4B, pharmacological inhibition of USP14 caused a dose-dependent inhibition of cell viability in endometrial cancer cell lines with an IC50 of 182.3 and 117.5 nM for HEC155 (left panel) and ECC1 (right panel), respectively.

Figure 4C:
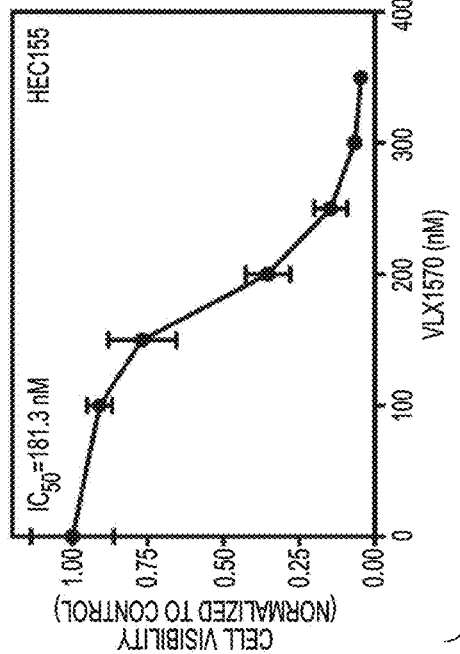
Figure 4C:
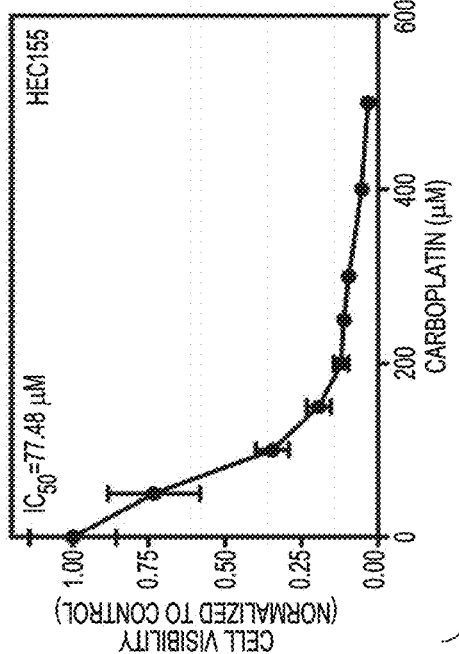

In the clinical setting, recurrent endometrial cancer is usually resistant to chemotherapy. Previous studies have reported that among endometrial cancer cell lines, HEC155 and ECC1 have the highest levels of LCAM, a marker for endometrial cancer recurrence [7, 19]. This suggests that these cell lines are appropriate in vitro models for more aggressive endometrial cancer. This is consistent with earlier reports indicating that the ECC1 cell line has a high degree of resistance to both cisplatin and carboplatin in vitro [20]. Thus, the $IC_{50}$ levels for carboplatin treatment of HEC155 and ECC1 cells was measured. As shown in FIG. 4C, the $IC_{50}$ levels for carboplatin were 77.48 and 97.58 μM for HEC155 (left panel) and ECC1 (right panel) respectively. Taken together this suggests a concentration-dependent anti-proliferative effect of the USP14 inhibitor VLX1570 in endometrial cancer cells at concentrations that are 500 and 800 times lower than that required for carboplatin.

Inhibition of USP14 Severely Compromises Ubiquitin-Dependent Protein Degradation in Endometrial Cancer Cells.

Figure 5A:
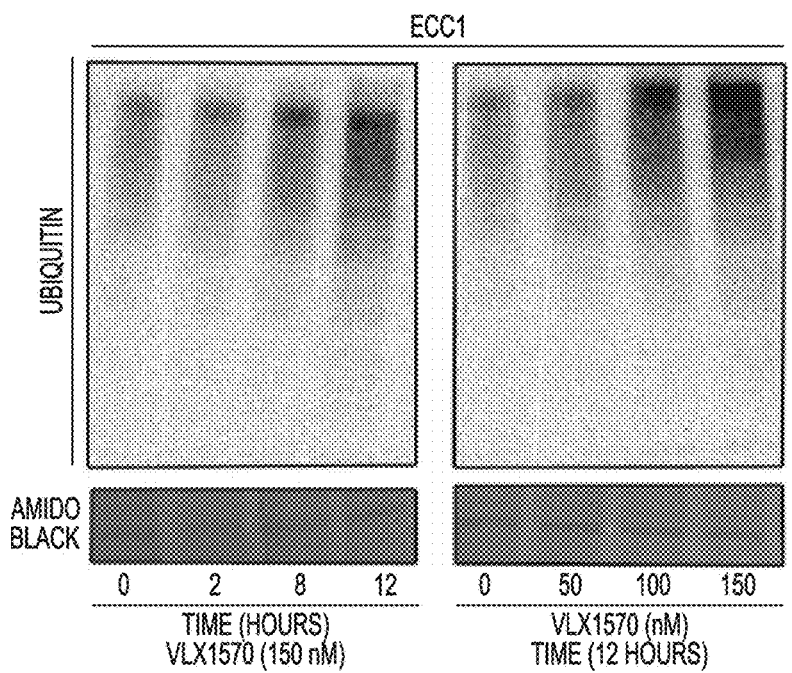
FIG. 5A-D depict time and dose-dependent effects of USP14 inhibition on degradation of ubiquitinated proteins. A. Time- (left panel) and dose-dependent (right panel) effects of VLX1570 treatment on the accumulation of poly-ubiquitinated proteins in the ECC1 endometrial cancer cell line. B. Quantification of the ubiquitin/amido black ratios for time- (top panel) and dose-dependent (bottom panel) VLX1570 treatment. C, Time- (left panel) and dose-dependent (right panel) effects of VLX1570 treatment on the accumulation of poly-ubiquitinated proteins in the HEC155 endometrial cancer cell line. D, Quantification of the ubiquitin/amido black ratios for time- (top panel) and dose-dependent (bottom panel) VLX1570 treatment.
Figure 5B:
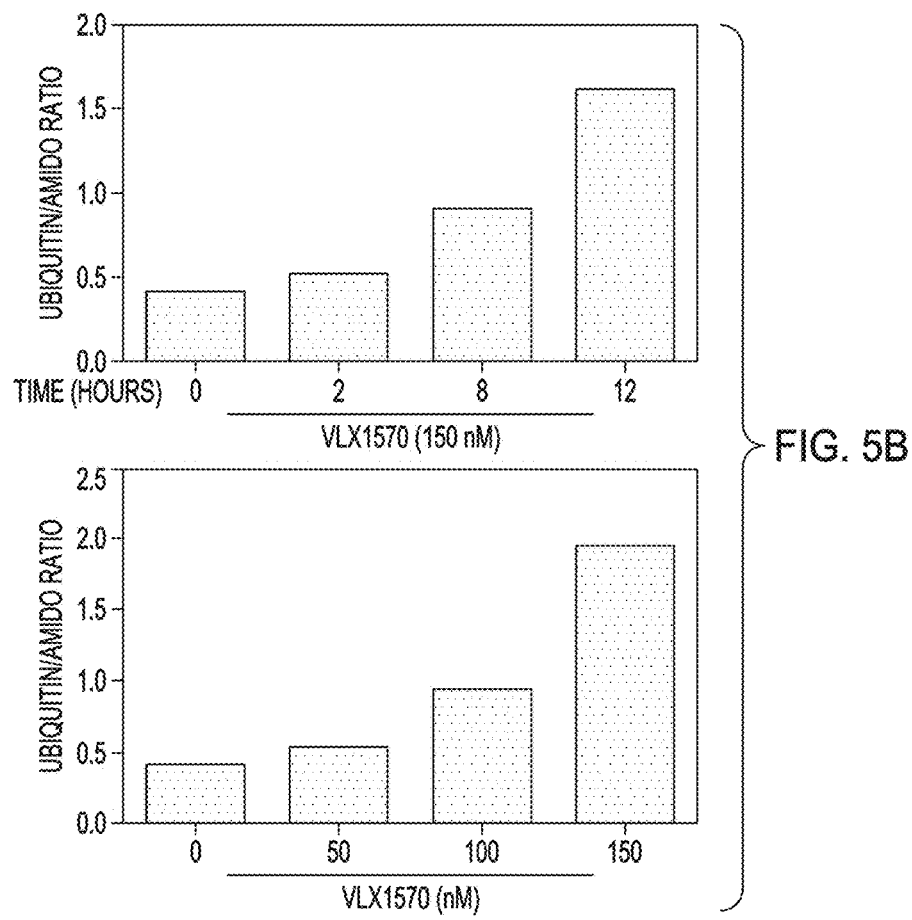
Figure 5C:
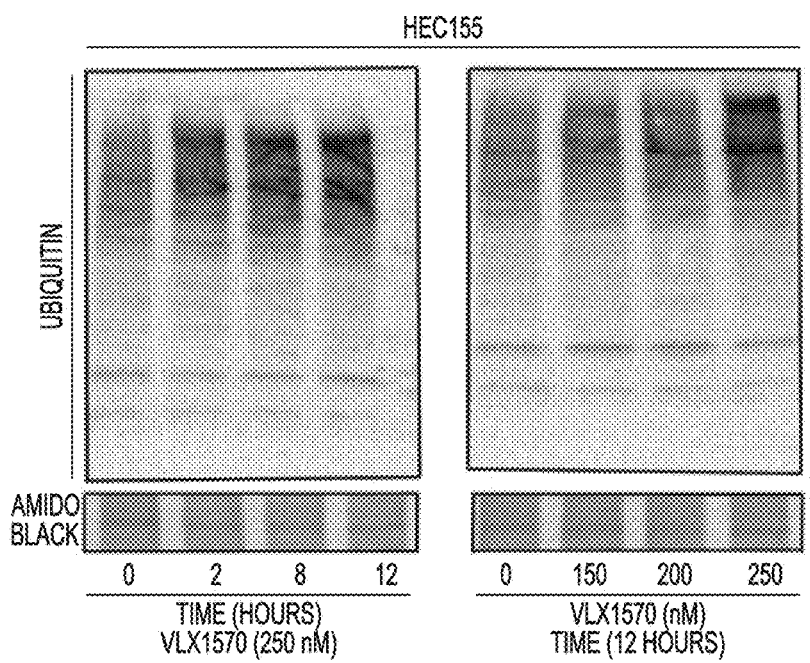
Figure 5D:
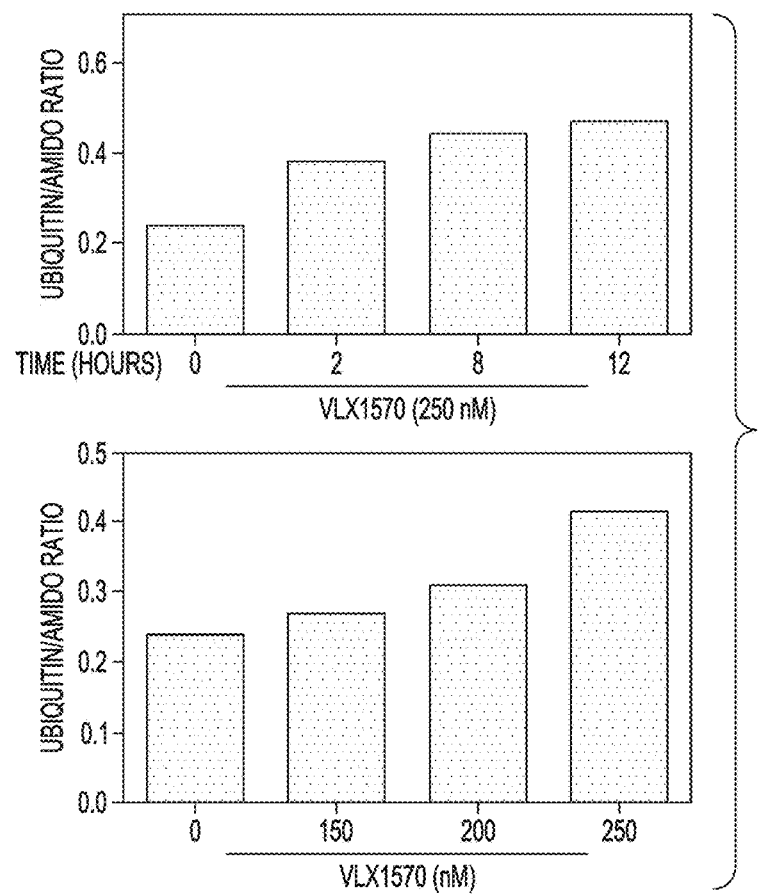

USP14 is a proteasome-associated deubiquitinating enzyme whose role is to remove ubiquitin molecules from targeted proteins prior to degradation by the 20S catalytic activities of the proteasome. Aggressive endometrial cancer cells express abnormally high levels of USP14 in situ suggesting a higher requirement for deubiquitinating activity. Thus, the consequences of USP14 inhibition on ubiquitin-dependent protein degradation in endometrial cancer cells was investigated. To this end, ECC1 and HEC155 cells were exposed to 150 nM or 250 nM VLX1570, respectively, over a period of 24 hours and the effect on cellular protein ubiquitination was evaluated by Western blot analysis after 0, 2, 8 or 12 hours from drug exposure. As shown in FIGS. 5A and 5C (left panels) VLX1570 treatment resulted in a dose-dependent accumulation of poly-ubiquitinated proteins in ECC1 and HEC155 cell lines starting as early as two hours from drug exposure. Quantifications of the changes in high molecular weight ubiquitin species in each respective cell line, versus control, are given in FIGS. 5B and 5D (top panels).

Next, endometrial cancer cell lines were exposed to increasing concentrations of VLX1570 (0-150 or 0-250 µM for ECC1 and HEC155, respectively) over a period of 24 hours. The effect on accumulation of poly-ubiquitinated proteins was evaluated by Western blot. As shown in FIGS. 5A and 5C (right panels), drug treatment resulted in a dose-dependent inhibition of ubiquitin-dependent protein degradation in endometrial cancer cells. Quantifications of the changes in high-molecular weight ubiquitin species in dose-dependent fashion are given in FIGS. 5B and 5D (bottom panels). Taken together, these data suggest that the loss of cell viability followed by inhibition of USP14 is accompanied by the inability of endometrial cancer cells to cope with increasing levels of proteotoxic stress.

USP14 Inhibition Induces G2-M Cell Cycle Arrest and Caspase-Mediated Apoptosis in Endometrial Cancer Cells.

Figure 6A:
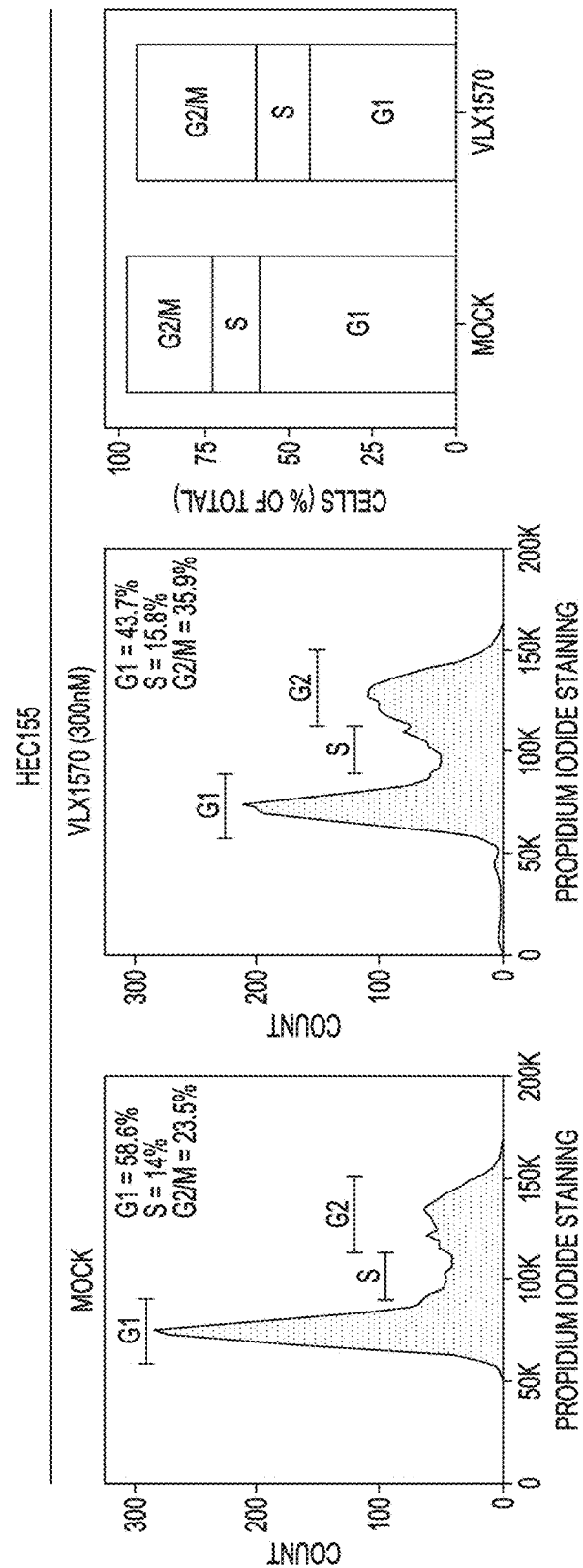
FIGS. 6A-B demonstrate that USP14 inhibition induces G2-M cell cycle arrest in endometrial cancer cells. A, HEC155 endometrial cancer cell line mock (left panel) or VLX1570 treated (middle panel) for 24 hours prior to propidium iodide staining and flow cytometric analysis to determine their cell cycle distribution. Insets correspond to percentage of cells in G1, S, and G2/M phases of the cell cycle. Right panel graphical representation of cell cycle distribution in control versus VLX1750 treated cells. B. EEC1 endometrial cancer cell line mock (left panel) or VLX treated (middle panel) for 24 hours prior to propidium iodide staining and flow cytometric analysis to determine their cell cycle distribution. Insets correspond to percentage of cells in G1, S, and G2/M phases of the cell cycle. Right panel, graphical representation of cell cycle distribution in control versus VLX1750 treated cells.
Figure 6B:
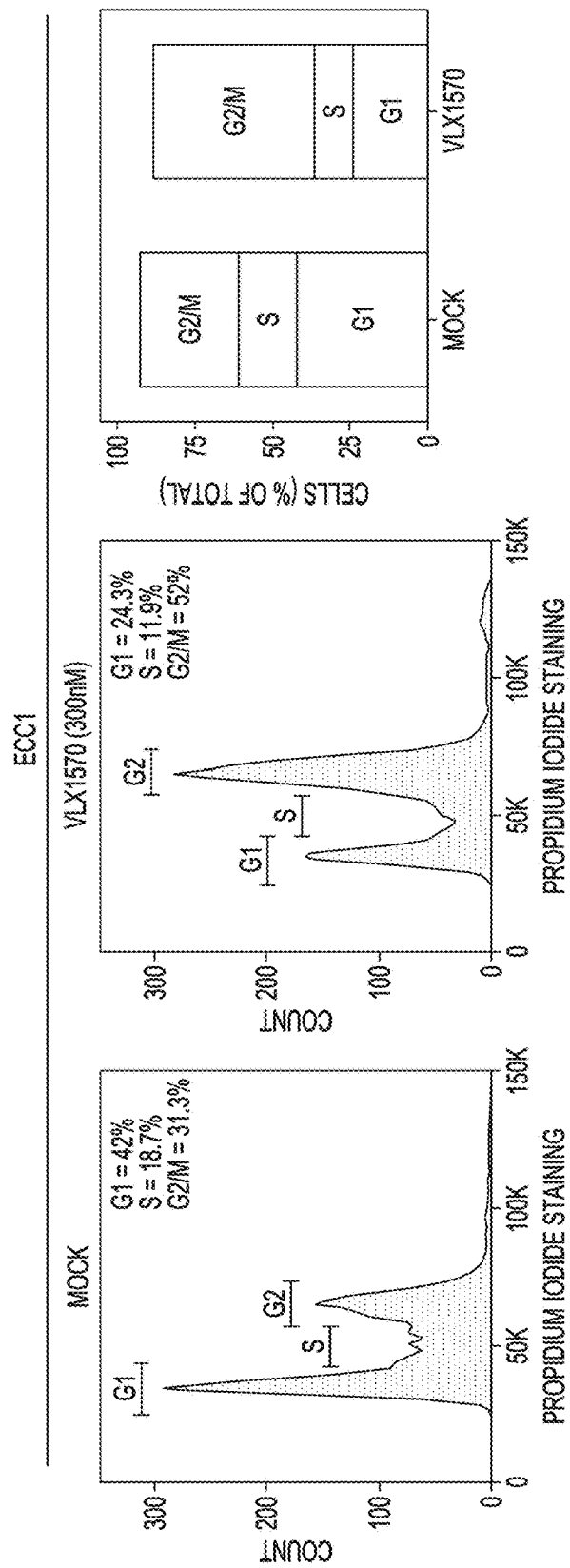

The USP14 modulates levels of cell cycle regulatory proteins whose dysregulation is expected to affect the cell cycle [21]. This is further supported by the findings showing a strong correlation between USP14 and Ki67 staining in clinical specimens of endometrial cancer. Thus, the hypothesis that inhibition of USP14 would result in endometrial cancer cells failing to progress through the cell cycle was tested. To this end, HEC155 and ECC1 endometrial cancer cells were incubated with the USP14 inhibitor VLX1570 over a period of 24 hours and the cell cycle status was analyzed by flow cytometry after staining with propidium iodide. It was found that treatment with 300 nM VLX1570 resulted in a shift in the cell cycle distribution in both endometrial cancer cell lines tested. Specifically, treatment of HEC155 cells led to an increase in the percentage of cells in the G2/M phase of the cell cycle as compared to controls (FIG. 6A). Likewise, the percentage of ECC1 cells in the G2/M phase of the cell cycle nearly double in treated versus control cells (FIG. 6B). Taken together, these results suggest that blocking USP14 activity impedes the cells progression through the cell cycle, arresting them in the G2/M phase.

Figure 7A:
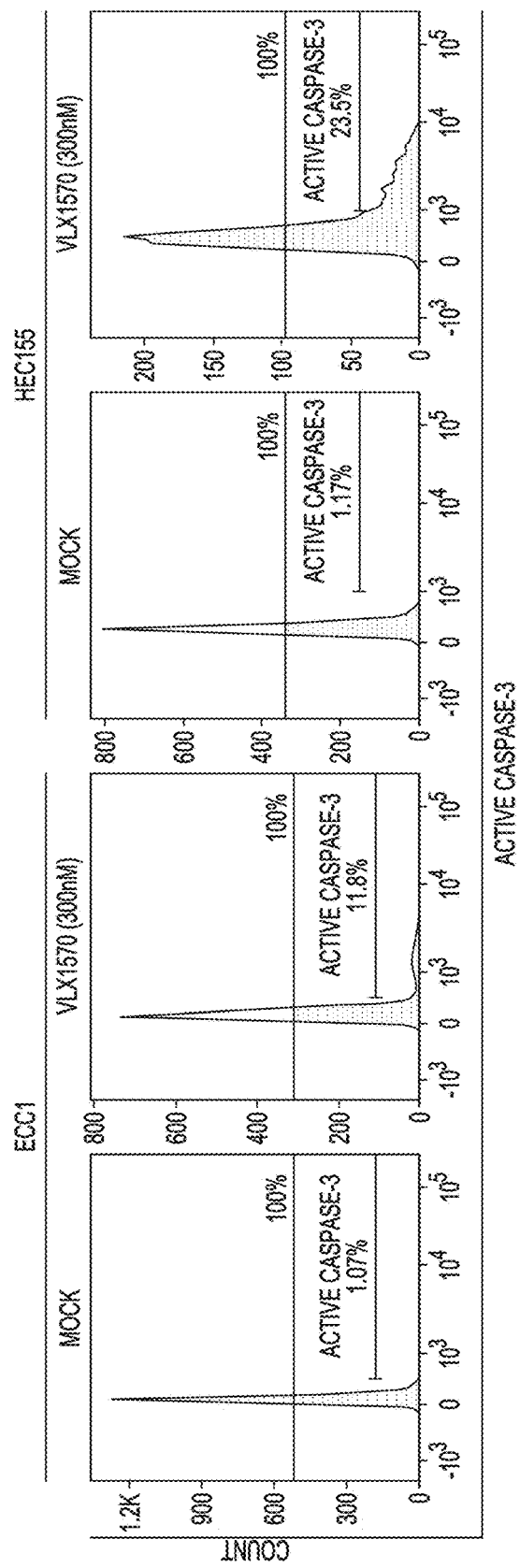
FIGS. 7A-B show that reduction of cell viability in endometrial cancer cell lines exposed to VLX1570 is consistent with apoptosis-mediated cell death. A. ECC1 (left panel) and HEC155 (right panel) endometrial cancer cells were mock or VLX1570 treated over a period of 24 hours. The cells were harvested, fixed and stained for the active form of Caspase-3. The percentage of cells within each gate is indicated. B, ECC1 (left panel) and HEC155 (right panel) endometrial cancer cells were mock or VLX1570 treated over a period of 24 hours. The cells were harvested and stained for DNA content (propidium iodide) and Annexin-V. The percentage of cells within each gate is indicated. The quadrants represent living cells (Q4), early apoptosis (Q3), late apoptosis (Q2) and necrosis (Q1).

Next, the fate of ECC1 and HEC155 endometrial cancer cells following VLX1570-induced cell cycle arrest was evaluated. Specifically, it was tested whether the reduction in cell viability following drug treatment is consistent with onset of apoptosis. The expression levels of active caspase-3 in control versus VLX1570 treated cells was measured. Importantly, caspase-3 is an active cell-death protease involved in the execution phase of apoptosis, where cells undergo morphological changes such as DNA fragmentation, chromatin condensation and apoptotic body formation. As shown in FIG. 7A, exposure to VLX1570 resulted in increased levels of active caspase-3 in both of the endometrial cancer cell lines tested.

Figure 7B:
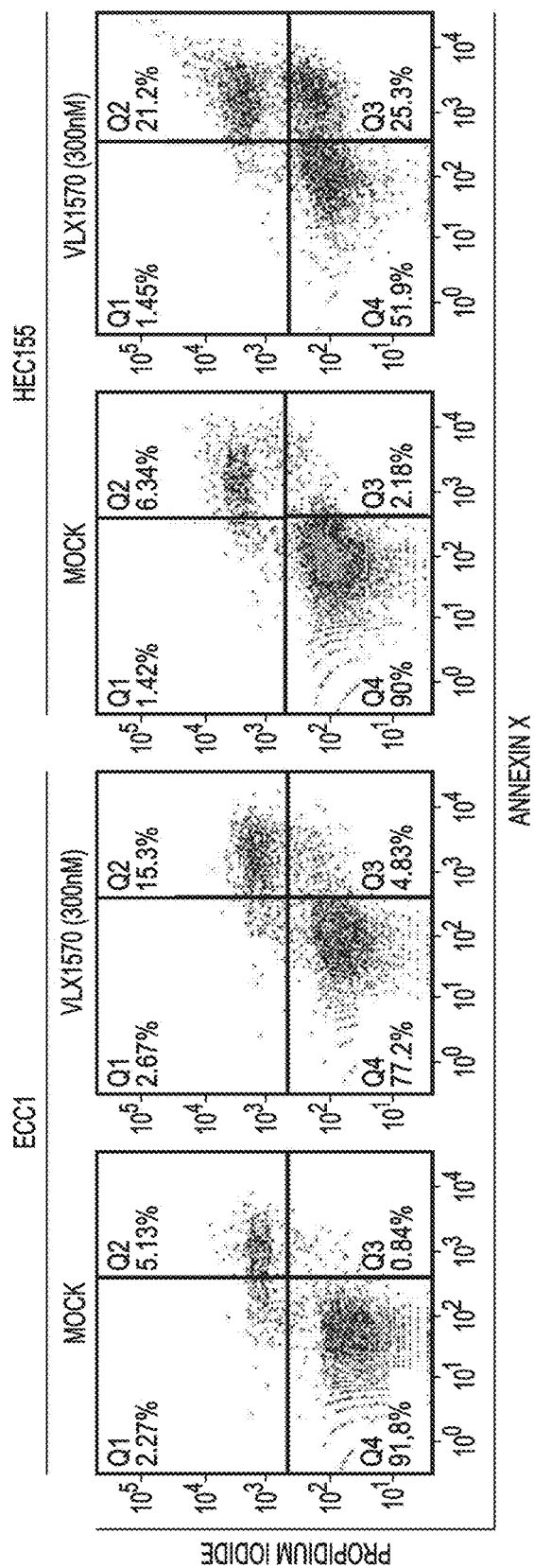

To further confirm this result, VLX1570-exposed ECC1 and HEC155 cells were analyzed by flow cytometry after staining with Annexin V. Annexin V protein specifically binds phosphatidylserine, a phospholipid normally localized on the inner leaflet of the plasma membrane which flips to the outer leaflet during early apoptotic signaling [21]. As shown in FIG. 7B, treatment with 300 nM VLX1570 for 24 hours resulted in an increase of Annexin V staining cells in control versus treated cells. Similarly, the fraction of cells taking up propidium iodide, a feature of both advanced apoptosis and necrosis, is elevated in controls versus treated cells. These findings support the hypothesis that pharmacological inhibition of USP14 triggers apoptosis in endometrial cancer cells.

USP14 is co-expressed with ETM makers during the multi-stage process leading to chemoresistance. Acquisition of aggressive phenotype and chemoresistance is a multi-stage process whereby the subpopulation of cells surviving drug treatment give rise to cells characterized by increased in migratory behavior, proliferation rate and chemoresistance via a transition accompanied by increase in stem cell and epithelial-mesenchymal transition (EMT) markers. This model was recapitulated in ECC1 endometrial cancer cell line and the temporal USP14 expression was evaluated during this multi-step process. Specifically. ECC1 cells were exposed to two rounds of carboplatin treatment (20 µM) over the period of two weeks. The first round resulted with approx. 60% of cell death. The second round resulted with approx. 90% of cell death. Consistent with what previously shown, the surviving population was characterized by giant, polyploidy, chemoresistant cells whose numbers remained similar over the course of the following two weeks. Consistent with what previously shown, this population was also the precursor of clones of proliferating and chemoresistant cells which had an IC50>3-fold as compared to the initial population. Next, the expression levels of USP14 and the EMT marker vimentin were evaluated in the initial population (chemosensitive tumor) and in two of the chemoresistant clones. USP14 overexpression is temporally associated to the expression of the EMT marker vimentin. Collectively these data that that USP14 plays a role during the EMT transition that leads to chemoresistance.

Discussion

While most women with early-stage endometrial adenocarcinoma have a favorable prognosis, a subset unexpectedly experience recurrence. In the current study, over 70% of women who recurred had endometrioid histology. This underlies the fundamental challenge in the management of early stage low-risk endometrial cancer where developments of clinically applicable prognostic markers are needed. It was found that higher USP14 expression levels were independently associated with recurrence and importantly added predictive value even when disease grade was known. This suggests a role for USP14 in predicting those who are at higher risk for recurrence and implications for clinical care.

One potential role for USP14 is in the preoperative setting to help determine the extent of surgical staging necessary for a given patient. Pelvic and periaortic lymph node dissection is considered part of the standard staging procedure for endometrial adenocarcinoma but carries a risk of intraoperative complications as well as risks for debilitating postoperative complications including lymphedema. Due to the morbidity associated with lymph node dissection, some gynecologic oncologists forego this procedure when operating on patients deemed to be low risk for advanced stage disease. The Mayo criteria is one model for reducing surgical morbidity and cost of medical care in low risk endometrial cancer but is limited by availability of intraoperative pathology [4]. Further study is needed; however. USP14 staining at the time of endometrial biopsy may support pre-operative surgical planning for women with endometrial cancer. In addition to guiding surgical decisions, establishing whether a patient is at greater risk for recurrence can also change recommendations regarding adjuvant therapy and surveillance.

USP14 can also serve as a therapeutic target. The data show a strong positive correlation between the intensity of USP14 staining and degree of proliferation as measured by Ki67 staining in clinical specimens of endometrial cancer in situ. This, along with previously published reports showing that USP14 expression levels fluctuate within cancer cells as they progress through the cell cycle [12], suggests that highly proliferating cells may have greater dependence on USP14 activity. Further, the data showed that pharmacological inhibition of USP14 with the FDA approved inhibitor VLX1570 [13, 22-26] was accompanied by a reduction of the cell viability of endometrial cancer cells with resistance to carboplatin. This is consistent with the knowledge that inhibition of the ubiquitin-dependent protein degradation pathway upstream of 20S proteasome has been shown to reverse chemoresistance to DNA damaging agents as well as 20S proteasome inhibitors in a number of cancer settings, possibly via restoring expression levels of pro-apoptotic proteins including MCL1 [27-29].

Cell cycle is a tightly regulated event under the control of numerous cyclins, cyclin-dependent kinases, and checkpoint proteins which are client proteins of the ubiquitin-proteasome-system. Specifically, pharmacological inhibition of USP14 as well as its genetic silencing has been shown to result in accumulation of high-molecular weight client proteins including cyclin A and B, suggesting that USP14 activity may be needed to regulate their steady-state levels [30-32]. This is consistent with the data herein indicating that reduction in cell viability following VLX1570 exposure is preceded by accumulation of the cells in G2-M. This is also consistent with activation of caspase-3 mediated apoptosis following VLX1570 exposure as a consequence of the inability of endometrial cancer cells to progress through anaphase [33].

USP14 is a biomarker for recurrent disease and inhibition of USP14 is of therapeutic benefit for women with endometrial adenocarcinoma.

BIBLIOGRAPHY

1. Howlader N, et al. (2014). SEER Cancer Statistics Review. 1975-2012. In: Institute NC, ed. (Bethesda, Md.).
2. Creasman W T, et al. Int J Gynaecol Obstet. 2006; 95 Suppl 1:S105-143.
3. Boll D, et al. Eur J Obstet Gynecol Reprod Biol. 2013; 166(2):209-214.
4. Dowdy S C, et al. Gynecologic oncology. 2012; 127(1):5-10.
5. Keys H M. et al. Gynecologic oncology. 2004; 92(3):744-751.
6. Bokhman J V. Gynecologic oncology. 1983; 15(1):10-17.
7. Zeimet A G, et al Journal of the National Cancer Institute. 2013; 105(15): 1142-1150.
8. Schirmer U. et al. BMC cancer. 2013; 13:156.
9. Creutzberg C L, et al. J Clin Oncol. 2004; 22(7):1234-1241.
10. Shinji S, et al. Oncology reports. 2006; 15(3):539-543.
11. Wu N. et al. International journal of molecular sciences. 2013; 14(6): 10749-10760.
12. Wang Y, et al. Medical oncology. 2015; 32(1):379.
13. Tian Z, et al. Blood. 2014; 123(5):706-716.
14. Wu N, et al. Cellular physiology and biochemistry: international journal of experimental cellular physiology, biochemistry, and pharmacology. 2014; 33(2):457-467.
15. Coughlin K, et al. Clinical cancer research: an official journal of the American Association for Cancer Research. 2014; 20(12):3174-3186.
16. Vogel R I, et al. Oncotarget. 2015; 6(6):4159-4170.
17. Stuart-Harris R, et al. Breast. 2008; 17(4):323-334.
18. de Azambuja E, et al. Br J Cancer. 2007; 96(10):1504-1513.
19. Huszar M, et al. The Journal of pathology. 2010; 220(5):551-561.
20. Nguyen H, et al. International journal of oncology. 1993; 3(2):375-382.
21. Bazzaro M, et al. Clinical cancer research: an official journal of the American Association for Cancer Research. 2008; 14(22):7340-7347.
22. Wang X, et al. Chemical biology & drug design. 2015; 86(5):1036-1048.
23. Sarhan D, et al. Cancer immunology, immunotherapy: CII. 2013; 62(8):1359-1368.
24. D'Arcy P, et al. Nature medicine. 2011; 17(12):1636-1640.
25. D'Arcy P and Linder S. 2012; 44(11):1729-1738.
26. Feng X, et al. Experimental hematology. 2014; 42(3): 172-182.
27. Hogarty M D. Cell research. 2010; 20(4):391-393.
28. Opferman J T and Green D R. Cancer cell. 2010; 17(2):117-119.
29. Schwickart M, et al. Nature. 2010; 463(7277):103-107.
30. Liu Y L, et al. Gene. 2015; 572(1):49-56.
31. Hu J, et al. Lung cancer. 2015; 88(3):239-245.
32. Fournane S. et al. Genes & cancer. 2012; 3(11-12):697-711.
33. Benanti J A. 2012; 23(5):492-498.
34. Pecorelli S. Int J Gynaecol Obstet. 2009; 105(2):103-104.
35. Sueblinvong T. et al. PLoS One. 2012; 7(11):e50519.
36. Anchoori R K, et al. PLoS One. 2011; 6(8):e23888.
37. DeLong E R, et al. Biometrics. 1988; 44(3):837-845.

Example 2—USP14 is a Predictor of Recurrence in Ovarian Cancer and a Molecular Target for Ovarian Cancer Treatment Endometrial cancer, serous and clear cell types are at increased risk for recurrence. Because similar treatment algorithm is utilized among serous and clear cell endometrial and ovarian cancers, this suggests that recurrent endometrial cancer and ovarian cancer share a similar biology. The important lesson from endometrial cancer is that tumor markers indicative of recurrent endometrial cancer can be predictive of increased risk for ovarian cancer recurrence.

Inhibition of USP14 selectively kills ovarian cancer cell lines resistant to cisplatin and primary ovarian cancer cells derived from patients with recurrent and chemoresistant disease. Sensitivity to inhibition of USP14 was evaluated in exponentially growing human fibroblasts, in the exponentially growing cisplatin resistant ovarian cancer cell lines HEY and OVCA-3 and in two exponentially growing primary cells derived from patient with recurrent and resistant (to carboplatin) disease. Primary cells were obtained according to a method recently described in two manuscripts.

Figure 8A:
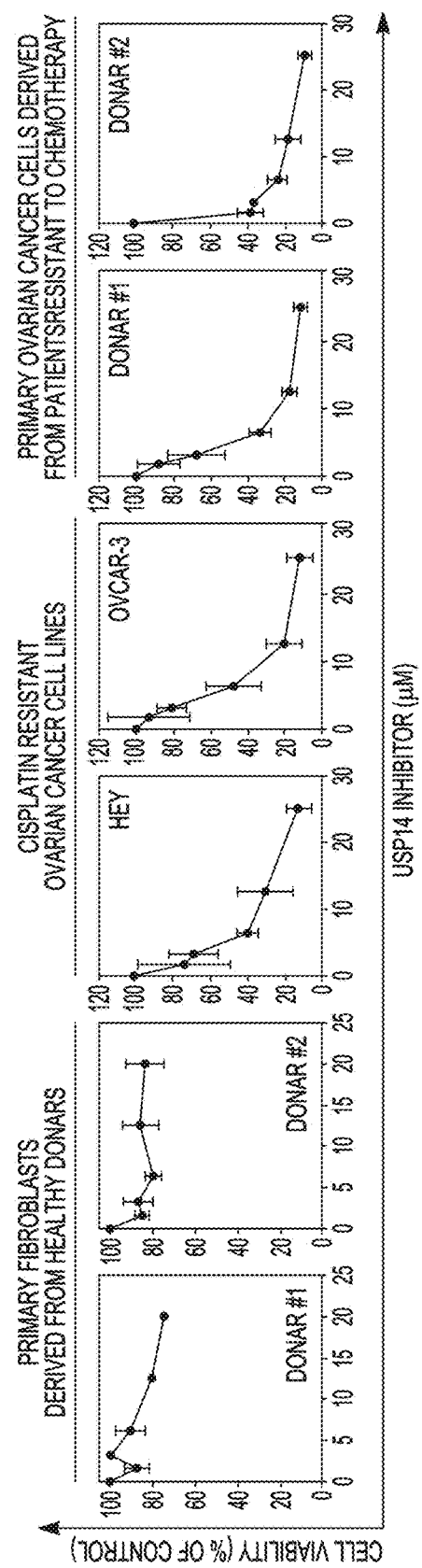
FIG. 8 shows the effect USP14 inhibition (with the small-molecule inhibitor RA-9; (3E, 5E)-3,5-bis(nitrobenzylidene)piperidin-4-one) upon fibroblast and ovarian cancer cells. A, Cell viability of cells exposed to increasing concentrations of RA-9 over a period of 48 hours. B, Measurement of active-caspase 3 levels in ovarian cancer cells exposed to increasing concentrations of RA-9.
Figure 8B:
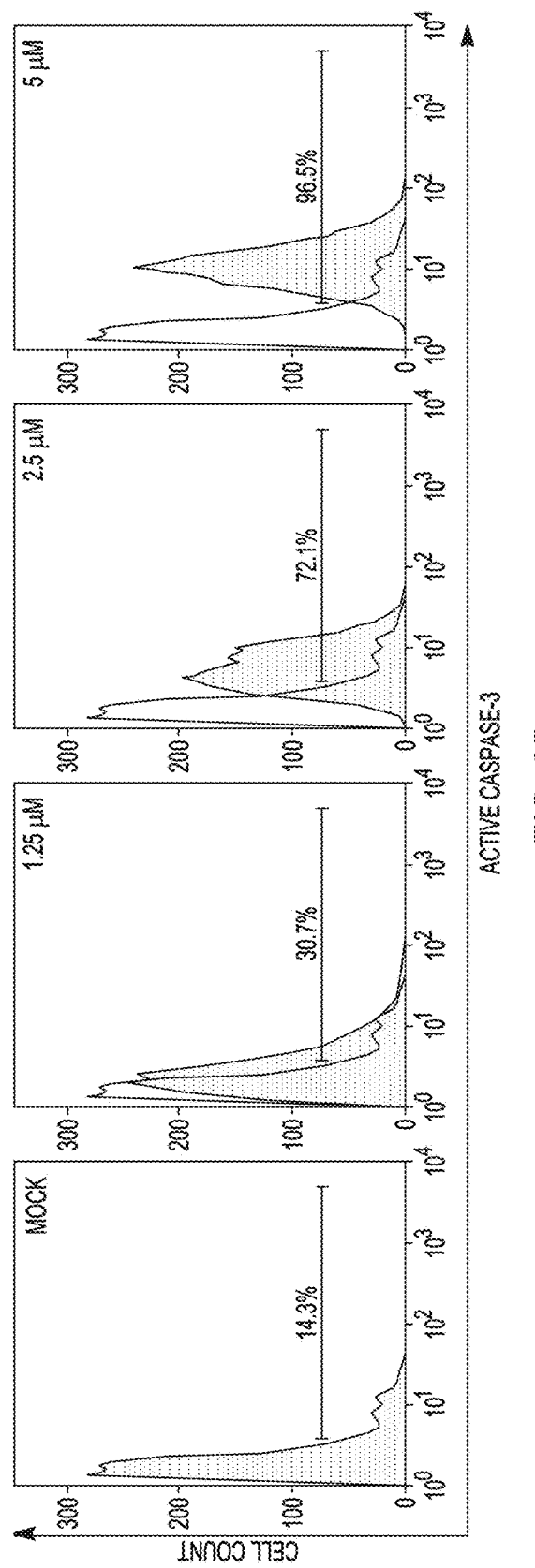

As shown in FIG. 8, exposure to increasing concentrations of USP14 inhibitor over a period of 48 hours killed chemoresistant ovarian cancer cells (cell lines and primary) with no significant effect proliferating fibroblasts and via a mechanism involving activation of Caspase-311. Taken together this suggests that USP14 inhibition is not toxic on normal cells, kills cells that do not respond to conventional chemotherapy regimens and that the decrease in cell viability, (as measured by XTT assay) in cancer cells, is consistent with onset of apoptosis. Preclinical evaluation of USP14 inhibition with a VLX1570 analogue, results with decrease tumor burden and increased overall survival in a xenograft model of ovarian cancer.

Figure 9A:
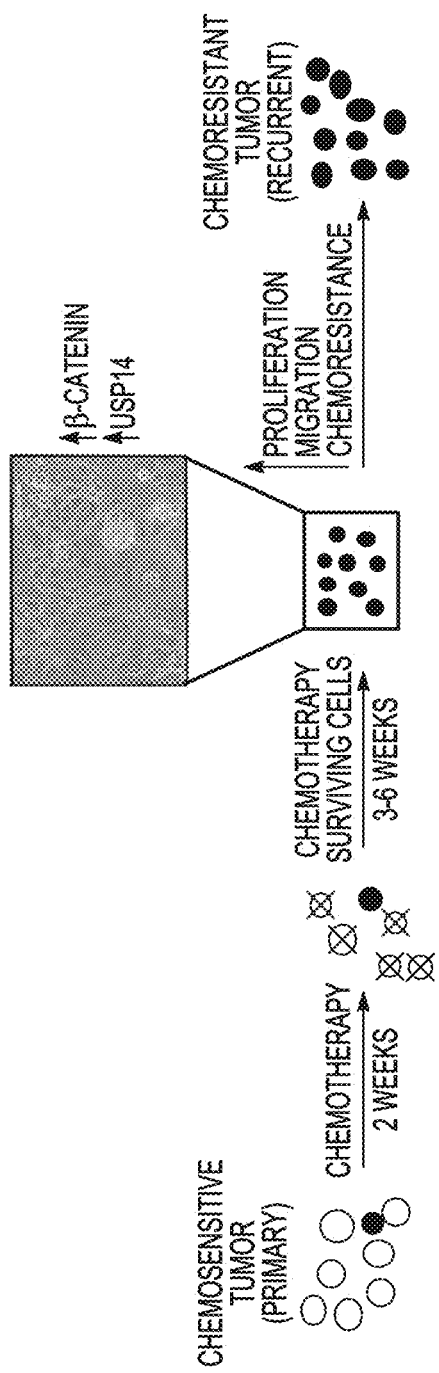
FIGS. 9A-B. USP14 is overexpressed along with the marker of β-catenin activation vimentin in a multi-step model of chemoresistance. A. Primary, chemosensitive tumor. Following carboplatin treatment (2 weeks), a small population of cells survives and give rise to chemoresistant clones, B, chemoresistant clones over-expressing USP14 and the vimentin marker.
Figure 9B:
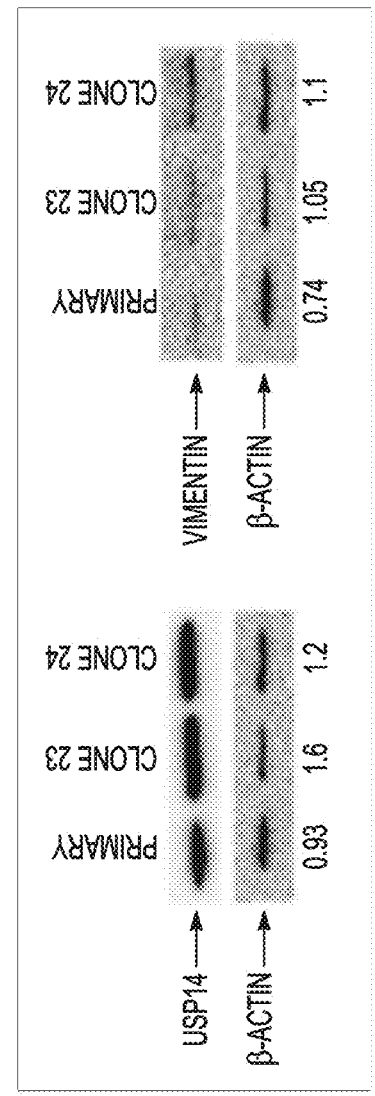

Multi-step process leading to recurrence can be recapitulated in vitro and results with up-regulation of USP14. Carboplatin chemoresistance was recapitulated in vitro according to the model schematized in FIG. 9. Specifically, carboplatin sensitive cancer cells were exposed to two rounds of carboplatin treatment (10 µM) over the period of two weeks. The first round resulted with approx. 60% of cell death. The second round resulted with approx. 90% of cell death. This is consistent with the dramatic reduction in tumor burden in chemosensitive patients treated with neoadjuvant chemotherapy. This suggests that this in vitro model recapitulates tumor behavior in patients with respect to sensitivity to chemotherapy. As shown in FIG. 9 the chemotherapy surviving population was characterized by stem like giant, polyploidy, chemoresistant cells whose numbers remained similar over the course of the following two weeks. This population was the precursor of clones of cells that survived in presence of carboplatin. Strikingly, when the expression levels of USP14 and the β-catenin marker vimentin were evaluated in the initial population (chemosensitive tumor) and in two of the chemoresistant clones isolated. USP14 overexpression is temporally associated to over-expression of the 3-catenin marker, vimentin. Taken together this strongly suggests that USP14 plays a role during chemoresistance and conceivably does so via regulation of the of the Wnt/betacatenin pathway.

Figure 10A:
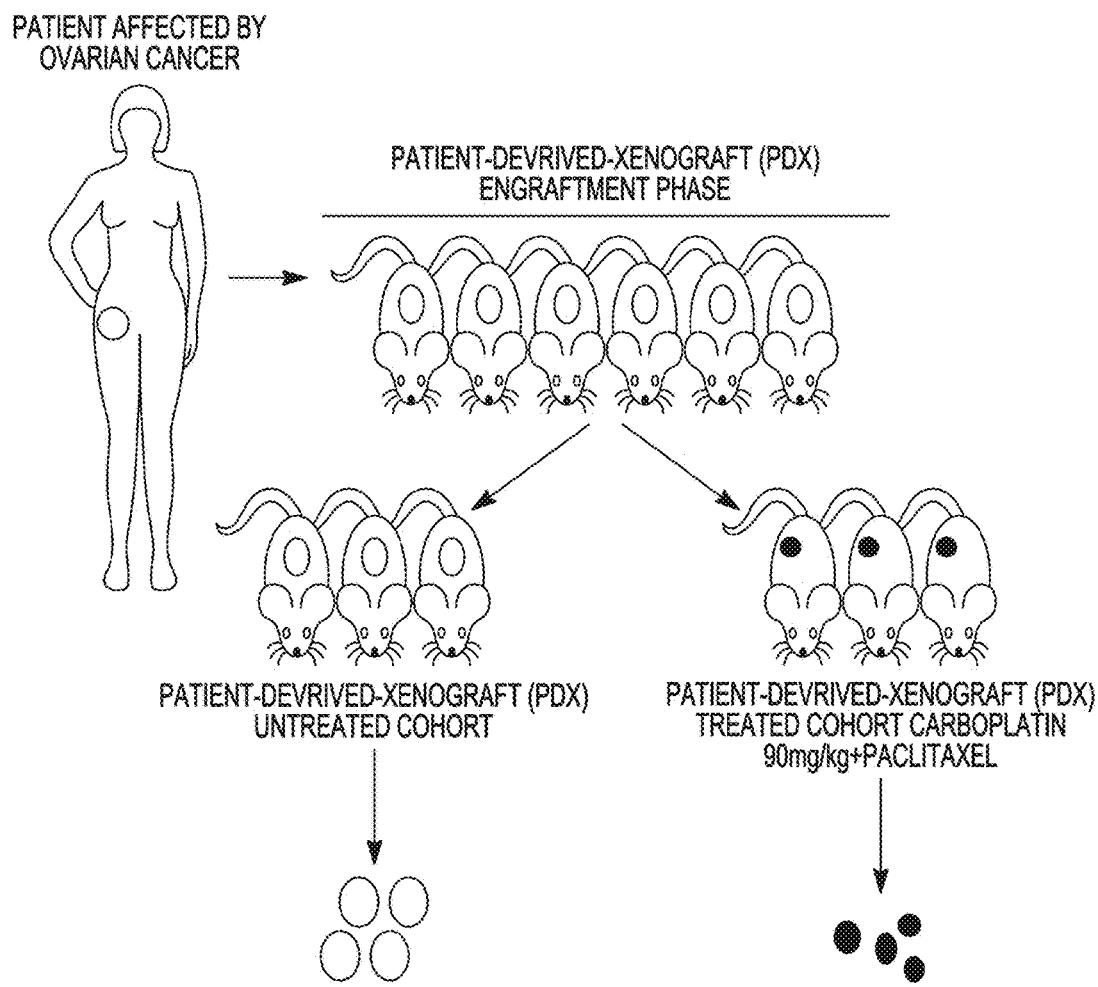
FIGS. 10A-B. The PDX model of ovarian cancer chemoresistance. A, Tumors are collected within minutes from debulking surgery, and implanted in nude mice. After tumors have established, they are either collected as untreated or treated with standard chemotherapy for ovarian cancer by mean of Carboplatin and Paclitaxel combination for 4 weeks. At the end of this treatment, the remaining tumor is now enriched for ovarian cancer cells that were not sensitive to chemotherapy constituting the chemoresistant population. B, tissue lysate from PDXs derived from 4 different patients (#1, #2, 3#, #4) subjected to Western blot analysis for USP14 expression. In pair from patients 1, 2 and 4 USP1 4 expression is higher in the chemoresistant tumor as compared to the matching chemosensitive. Red dot=chemosensitive Blue dot=chemoresistant.
Figure 10B:
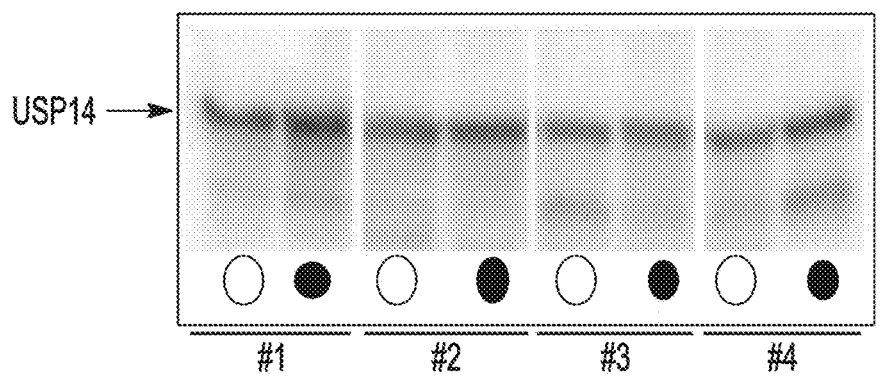

Multi-step process leading to chemoresistance can be recapitulated preclinically and results with up-regulation of USP14. It was tested whether USP14 is overexpressed in the chemoresistant Patient-Derived-Xenograft model of ovarian cancer. In this model tumors are harvested from ovarian cancer patients, implanted into female athymic mice and allowed to grow until approximately 1.5 cm in maximal dimension. At that time some tumors are collected as "untreated tumors." some are expanded into a second generation and treated with chemotherapy by means of carboplatin (90 mg/kg) and paclitaxel (20 mg/kg) weekly for 4 weeks. A scheme of this model is shown in FIG. 10A. Strikingly, the data using this model show that in 3 out of 4 PDX models obtained from three different patients diagnosed with high-grade serous carcinoma of the ovaries. USP14 is overexpressed in the chemoresistant versus the chemosensitive tumor from the same patient (FIG. 10B). Taken together this strongly suggests that chemoresistant ovarian cancer is more dependent upon USP14 as compared to chemosensitive tumors.

Figure 11:
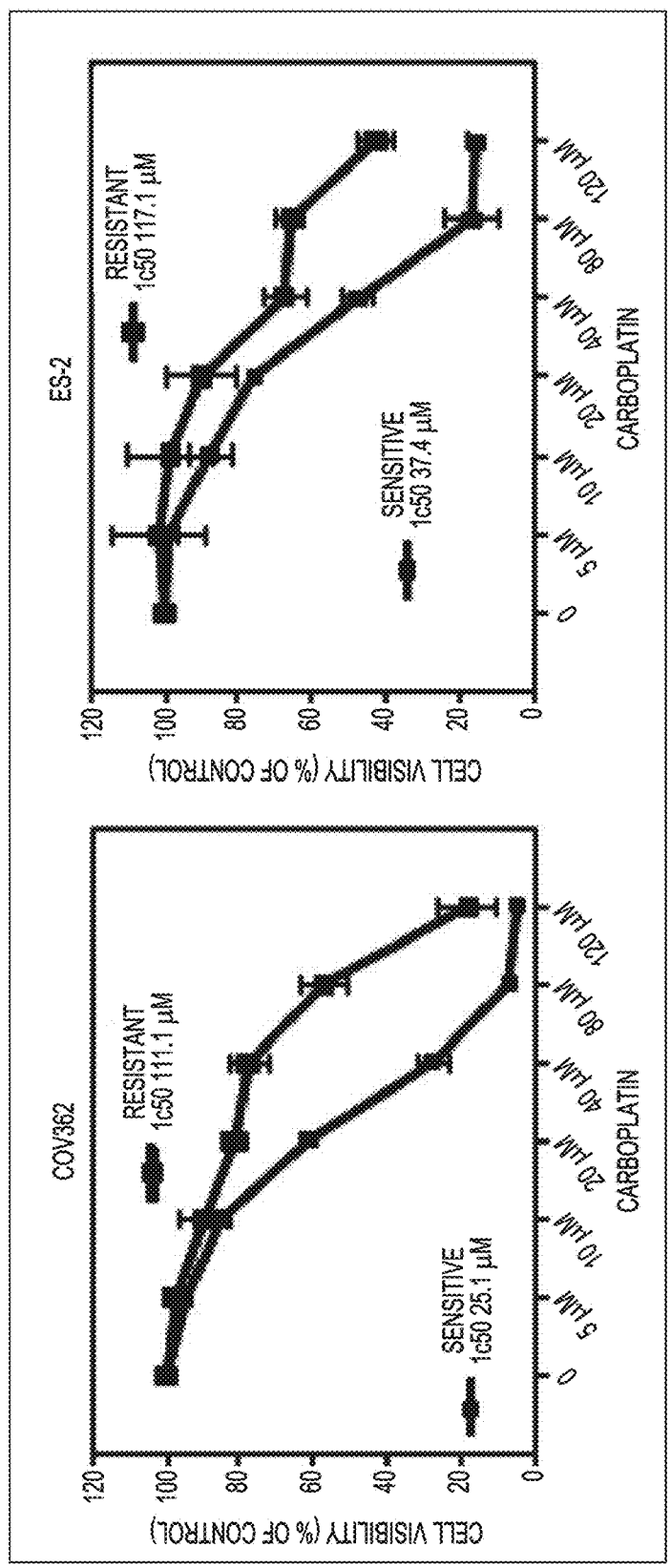
FIG. 11. COV362 and ES-2 carboplatin-resistant clones. Residual cell viability of sensitive and resistant COV362 and ES-2 ovarian cancer cells exposed to the indicated concentrations of carboplatin over a period of 48 hours.
Figure 12:
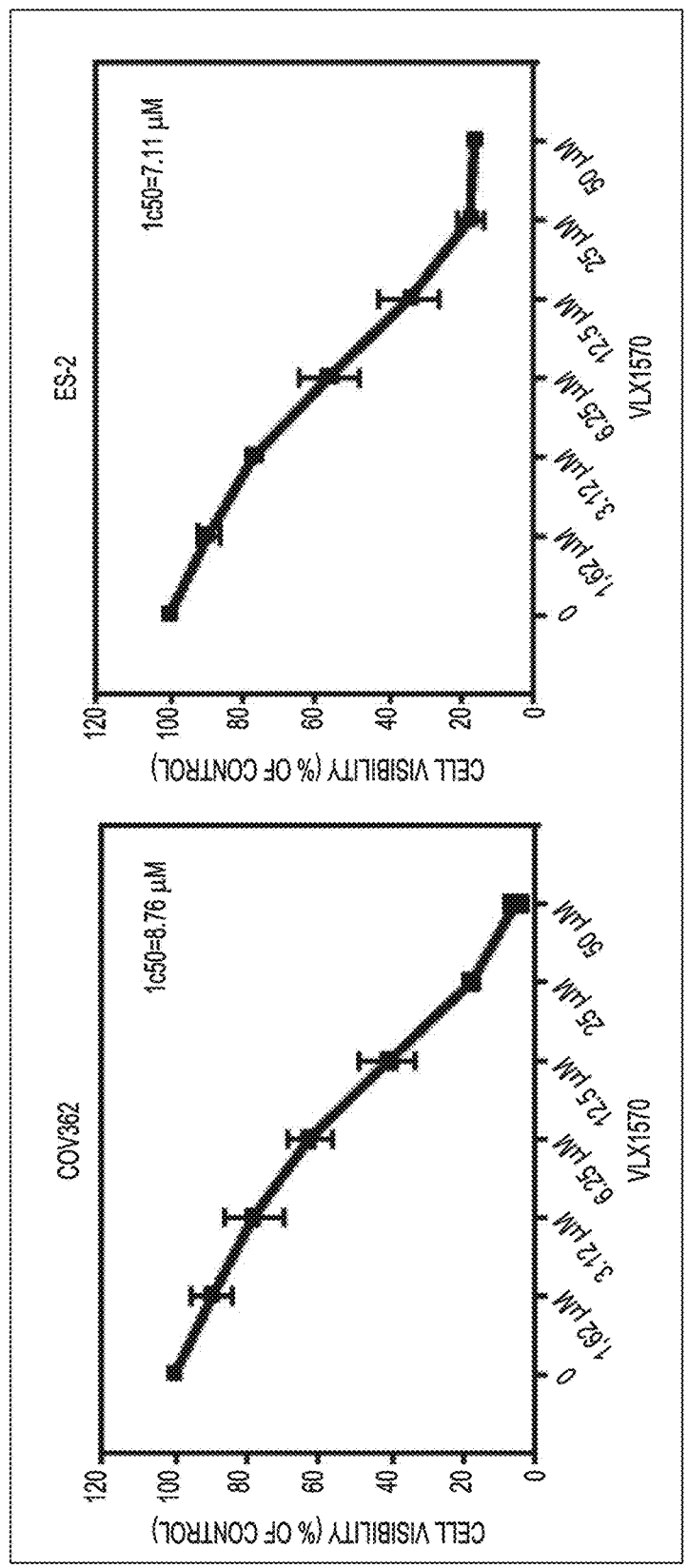
FIG. 12. Carboplatin resistant COV362 and ES-2 ovarian cancer cells are sensitive to USP14 inhibition. Residual cell viability of resistant COV362 and ES-2 ovarian cancer cells exposed to the indicated concentrations of the FDA approved USP14 inhibitor VLX1570 over a period of 48 hours. The structure of VLX1570 is.

Carboplatin-resistant ovarian cancer cell lines are sensitive to pharmacological inhibition of USP14. Two ovarian cancer cell lines, COV-362 and ES-2 were exposed to carboplatin according to the method described in FIG. 9 and the resulting USP14 overexpressing clones were subjected to cell viability assay to assess the extent of chemoresistance. As shown in FIG. 11, cell viability of either sensitive or resistant COV362 and ES-2 was assessed after 48 hours exposure to increasing concentrations of carboplatin and resulted with an a >4-fold and >3-fold decrease in carboplatin sensitivity for COV-362 and ES-2 respectively. Next, the sensitivity of COV362 and ES-2 resistant clones to the FDA approved USP14 inhibitor VLX1570 was determined. As shown in FIG. 12, exposure to VLX1570 over a period of 48 hours resulted with a dose dependent inhibition of cell viability of COV362 and ES-2 cell lines with $IC_{50}$ of 8.76 and 7.11 uM respectively. Taken together, this suggests that inhibition of USP14 kills ovarian cancer cells that are no longer sensitive to carboplatin and does so at concentrations that are approx. 10-fold lower than the one required with carboplatin.

BIBLIOGRAPHY

1. Jelovac D. Armstrong D K. Recent progress in the diagnosis and treatment of ovarian cancer. CA Cancer J Clin. 2011; 61(3):183-203.
2. Rohnalter V, Roth K. Finkernagel F. et al. A multi-stage process including transient polyploidization and EMT precedes the emergence of chemoresistent ovarian carcinoma cells with a dedifferentiated and pro-inflammatory secretory phenotype. Oncotarget. 2015; 6(37):40005-40025.
3. Ricci F. Bernasconi S, Perego P. et al. Ovarian carcinoma tumor-initiating cells have a mesenchymal phenotype. Cell Cycle. 2012; 11(10): 1966-1976.
4. Walters Haygood C L, Arend R C. Straughn J M, Buchsbaum D J. Ovarian cancer stem cells: Can targeted therapy lead to improved progression-free survival? World J Stem Cells. 2014; 6(4):441-447.
5. Steg A D. Bevis K S. Katre A A, et al. Stem cell pathways contribute to clinical chemoresistance in ovarian cancer. Clin Cancer Res. 2012; 18(3):869-881.
6. Gatcliffe T A. Monk B J, Planutis K, Holcombe R F. Wnt signaling in ovarian tumorigenesis. Int J Gynecol Cancer. 2008:18(5):954-962.
7. Takebe N. Harris P J, Warren R Q, Ivy S P. Targeting cancer stem cells by inhibiting Wnt. Notch, and Hedgehog pathways. Nat Rev Clin Oncol. 2011; 8(2):97-106.
8. Wend P. Holland J D, Ziebold U, Birchmeier W. Wnt signaling in stem and cancer stem cells. Semin Cell Dev Biol. 2010; 21(8):855-863.
9. Jung H, Kim B G. Han W H, et al. Deubiquitination of Dishevelled by Usp14 is required for Wnt signaling. Oncogenesis. 2013; 2:e64.
10. Wang Y. Wang J. Zhong J, et al. Ubiquitin-specific protease 14 (USP14) regulates cellular proliferation and apoptosis in epithelial ovarian cancer. Med Oncol. 2015; 32(1):379.
11. Coughlin K. Anchoori R, Iizuka Y, et al. Small-molecule RA-9 inhibits proteasome-associated DUBs and ovarian cancer in vitro and in vivo via exacerbating unfolded protein responses. Clin Cancer Res. 2014; 20(12):3174-3186.
12. Vogel R I. Pulver T. Heilmann W. et al. USP14 is a predictor of recurrence in endometrial cancer and a molecular target for endometrial cancer treatment. Oncotarget. 2016.
13. Wang X, Mazurkiewicz M, Hillert E K. et al. The proteasome deubiquitinase inhibitor VLX1570 shows selectivity for ubiquitin-specific protease-14 and induces apoptosis of multiple myeloma cells. Sci Rep. 2016; 6:26979.
14. Sueblinvong T, Ghebre R. Iizuka Y, et al. Establishment, characterization and downstream application of primary ovarian cancer cells derived from solid tumors. PLoS One. 2012; 7(11):e50519.

15. Pribyl L J, Coughlin K A, Sueblinvong T, et al. Method for obtaining primary ovarian cancer cells from solid specimens. J Vis Exp. 2014(84):e51581.
16. Mani S A, Guo W. Liao M J. et al. The epithelial-mesenchymal transition generates cells with properties of stem cells. Cell. 2008; 133(4):704-715.
17. Polyak K, Weinberg R A. Transitions between epithelial and mesenchymal states: acquisition of malignant and stem cell traits. Nat Rev Cancer. 2009; 9(4):265-273.
18. Lamouille S, Xu J. Derynck R. Molecular mechanisms of epithelial-mesenchymal transition. Nat Rev Mol Cell Biol. 2014; 15(3):178-196.
19. Carvalho M J, Laranjo M, Abrantes A M, Torgal I, Botelho M F, Oliveira C F, Clinical translation for endometrial cancer stem cells hypothesis. Cancer Metastasis Rev. 2015; 34(3):401-416.
20. Kato K. Endometrial cancer stem cells: a new target for cancer therapy. Anticancer Res. 2012; 32(6):2283-2293.
21. Kato K. Stem cells in human normal endometrium and endometrial cancer cells: characterization of side population cells. Kaohsiung J Med Sci. 2012; 28(2):63-71.
22. Dobbin Z C. Katre A A, Steg A D, et al. Using heterogeneity of the patient-derived xenograft model to identify the chemoresistant population in ovarian cancer. Oncotarget. 2014; 5(18):8750-8764.
23. Griffin P, Sexton A. Macneill L, Iizuka Y, Lee M K, Bazzaro M. Method for measuring the activity of deubiquitinating enzymes in cell lines and tissue samples. J Vis Exp. 2015(99):e52784.
24. Wang L, Chen Y J, Xu K, Wang Y Y, Shen X Z, Tu R Q, High expression of UCH37 is significantly associated with poor prognosis in human epithelial ovarian cancer. Tumour Biol. 2014; 35(11):11427-11433.
25. Arend R C, Londono-Joshi A I, Straughn J M, Jr., Buchsbaum D J. The Wnt/beta-catenin pathway in ovarian cancer: a review. Gynecol Oncol. 2013; 131(3):772-779.
26. Bagnato A. Rosano L. Understanding and overcoming chemoresistance in ovarian cancer: emerging role of the endothelin axis. Curr Oncol. 2012; 19(1):36-38.
27. Seton-Rogers S. Epithelial-mesenchymal transition: Untangling EMT's functions. Nat Rev Cancer. 2016; 16(1):1.
28. Kalluri R, Weinberg R A. The basics of epithelial-mesenchymal transition. J Clin Invest. 2009; 119(6): 1420-1428.
29. Lee J M, Dedhar S, Kalluri R. Thompson E W. The epithelial-mesenchymal transition: new insights in signaling, development, and disease. J Cell Biol. 2006; 172(7): 973-981.
30. Bodnar L. Stanczak A, Cierniak S, et al. Wnt/beta-catenin pathway as a potential prognostic and predictive marker in patients with advanced ovarian cancer. J Ovarian Res. 2014; 7:16.
31. Lee B H. Lee M J. Park S, et al. Enhancement of proteasome activity by a small-molecule inhibitor of USP14. Nature. 2010:467(7312): 179-184.
32. Lin Z, Bazzaro M, Wang M C. Chan K C, Peng S, Roden R B. Combination of proteasome and HDAC inhibitors for uterine cervical cancer treatment. Clin Cancer Res. 2009; 15(2):570-577.
33. Bazzaro M. Lin Z, Santillan A, et al. Ubiquitin proteasome system stress underlies synergistic killing of ovarian cancer cells by bortezomib and a novel HDAC6 inhibitor. Clin Cancer Res. 2008; 14(22):7340-7347.
34. Boone J D, Arend R C. Johnston B E. et al. Targeting the Wnt/beta-catenin pathway in primary ovarian cancer with the porcupine inhibitor WNT974. Lab Invest. 2016; 96(2):249-259.
35. Iizuka Y. Cichocki F, Sieben A, et al. UNC-45A Is a Nonmuscle Myosin IIA Chaperone Required for N K Cell Cytotoxicity via Control of Lytic Granule Secretion. J Immunol. 2015; 195(10):4760-4770.
36. Anchoori R K. Khan S R. Sueblinvong T. et al. Stressing the ubiquitin-proteasome system without 20S proteolytic inhibition selectively kills cervical cancer cells. PLoS One. 2011; 6(8):c23888.
37. Bazzaro M, Lee M K, Zoso A, et al. Ubiquitin-proteasome system stress sensitizes ovarian cancer to proteasome inhibitorinduced apoptosis. Cancer Res. 2006:66 (7):3754-3763.
38. Shah M M, Landen C N. Ovarian cancer stem cells: are they real and why are they important? Gynecol Oncol. 2014:132(2):483-489.
39. Davidson B, Trope C G, Reich R. Epithelial-mesenchymal transition in ovarian carcinoma. Front Oncol. 2012; 2:33.
40. Marchini S, Fruscio R, Clivio L, et al. Resistance to platinum-based chemotherapy is associated with epithelial to mesenchymal transition in epithelial ovarian cancer. Eur J Cancer. 2013; 49(2):520-530.
41. Nuti S V, Mor G, Li P, Yin G. TWIST and ovarian cancer stem cells: implications for chemoresistance and metastasis. Oncotarget. 2014:5(17):7260-7271.
42. Dontu G, Al-Hajj M, Abdallah W M, Clarke M F, Wicha M S. Stem cells in normal breast development and breast cancer. Cell Prolif. 2003; 36 Suppl 1:59-72.
43. Al-Hajj M, Wicha M S, Benito-Hernandez A, Morrison S J, Clarke M F. Prospective identification of tumorigenic breast cancer cells. Proc Natl Acad Sci USA. 2003; 100(7):3983-3988.
44. Collins A T, Berry P A, Hyde C, Stower M J, Maitland N J. Prospective identification of tumorigenic prostate cancer stem cells. Cancer Res. 2005; 65(23):10946-10951.
45. Ricci-Vitiani L, Lombardi D G, Pilozzi E, et al. Identification and expansion of human colon-cancer-initiating cells. Nature. 2007; 445(7123): 111-115.
46. Friel A M, Sergent P A, Patnaude C, et al. Functional analyses of the cancer stem cell-like properties of human endometrial tumor initiating cells. Cell Cycle. 2008; 7(2): 242-249.
47. Doll A, Gonzalez M, Abal M, et al. An orthotopic endometrial cancer mouse model demonstrates a role for RUNX1 in distant metastasis. Int J Cancer. 2009; 125(2): 257-263.
48. Haldorsen I S, Popa M, Fonnes T, et al. Multimodal Imaging of Orthotopic Mouse Model of Endometrial Carcinoma. PLoS One. 2015; 10(8):e0135220.
49. Wang X, D'Arcy P. Caulfield T R, et al. Synthesis and evaluation of derivatives of the proteasome deubiquitinase inhibitor b-AP15. Chem Biol Drug Des. 2015; 86(5):1036-1048.
50. Cheng H, Liu P, Zhang F, et al. A genetic mouse model of invasive endometrial cancer driven by concurrent loss of Pten and Lkb1 Is highly responsive to mTOR inhibition. Cancer Res. 2014; 74(1): 15-23.
51. Pearson A T, Finkel K A, Warner K A. et al. Patient-derived xenograft (PDX) tumors increase growth rate with time. Oncotarget. 2016.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method to selectively treat a subject at risk of recurring endometrial cancer, which comprises selectively administering to the subject an agent which inhibits the activity of USP14, on the basis of said subject having previously been determined to have increased expression of USP14 in said cancer as compared to a control.

2. The method of claim 1, wherein the agent is a protein, nucleic acid and/or small molecule.

3. The method of claim 2, wherein the small molecule is VLX1570 or RA-9.

4. The method of claim 1, further comprising surgery, chemotherapy, and/or radiation.

5. The method of claim 4, wherein the surgery comprises lymph node dissection.

6. The method of claim 1, wherein the cancer is chemoresistant.

* * * * *